US011649429B2

(12) United States Patent
Kumar et al.

(10) Patent No.: US 11,649,429 B2
(45) Date of Patent: May 16, 2023

(54) MUTANT ALGAL STRAIN AND METHODS THEREOF

(71) Applicant: Reliance Industries Limited, Maharashtra (IN)

(72) Inventors: Chitranshu Kumar, Navi Mumbai (IN); Bhaskar Bhadra, Telangana (IN); Niraja Soni, Maharashtra (IN); Saranya Karuppasamy, Tamil Nadu (IN); Shradha Khater, Maharashtra (IN); Venkata Subhash G, Andhra Pradesh (IN); Aniket A. Teredesai, Maharashtra (IN); Navish Kumar Batchu, Telangana (IN); Gurumurthy Raja Krishna Kumar, Maharashtra (IN)

(73) Assignee: Reliance Industries Limited, Mumbai (IN)

( * ) Notice: Subject to any disclaimer, the term of this patent is extended or adjusted under 35 U.S.C. 154(b) by 240 days.

(21) Appl. No.: 16/834,947

(22) Filed: Mar. 30, 2020

(65) Prior Publication Data

US 2020/0354670 A1 Nov. 12, 2020

(30) Foreign Application Priority Data

May 7, 2019 (IN) ............................ 201921018233

(51) Int. Cl.

*C12N 1/12* (2006.01)
*C07K 14/405* (2006.01)
*C12N 9/00* (2006.01)
*C12N 9/22* (2006.01)

(52) U.S. Cl.

CPC .............. *C12N 1/12* (2013.01); *C07K 14/405* (2013.01); *C12N 9/22* (2013.01); *C12N 9/93* (2013.01); *C12Y 603/04006* (2013.01)

(58) Field of Classification Search

CPC ... C12N 1/12; C12N 9/22; C12N 9/93; C12N 9/0071; C12N 9/20; C12N 15/01; C07K 14/405; C12Y 603/04006; C12Y 114/19; C12Y 301/01003; C12P 7/6427

See application file for complete search history.

(56) References Cited

U.S. PATENT DOCUMENTS

2018/0187170 A1* 7/2018 Negi ........................ C12N 9/12

OTHER PUBLICATIONS

Fan, C. et al. Crystal Structure of Urea Carboxylase Provides Insights into the Carboxyltransfer Reaction, 2012, Journal of Biological Chemistry, 287(12): 9389-9398 (Year: 2012).*

Zhuang, X-Y. et al. Key Enzymes in Fatty Acid Synthesis Pathway for Bioactive Lipids Biosynthesis, 2022, Frontiers in Nutrition, 9, Article 851402: 1-12 (Year: 2022).*

Sahoo, S. et al. Comprehensive sequence and structure analysis of algal lipid catabolic enzyme Triacylglycerol lipase: an in silico study to vitalize the development of optimum engineered strains with high lipid productivity, 2021, J Biomol Struct Dyn, PRMID: 34414234, 1-19 (Year: 2021).*

Christie, "Lipid Analysis: Isolation, Separation, Identification and Structural Analysis of Lipids," 3rd ed., The Oily Press, 2003, Book Review, 2 pages.

Kumar et al., "Lipid extraction methods from microalgae: a comprehensive review," Frontiers in Energy Research, Jan. 2015, 2(61):1-9.

Laurens et al., "Accurate and reliable quantification of total microalgal fuel potential as fatty acid methyl esters by in situ transesterification," Analytical and Bioanalytical Chemistry, Feb. 2012, 403(1):167-178.

Van Wychen et al., "Determination of Total Solids and Ash in Algal Biomass," National Renewable Energy Laboratory, retrieved from URL <https://www.nrel.gov/docs/fy16osti/60956.pdf>, Dec. 2013, 11 pages.

* cited by examiner

*Primary Examiner* — Louise W Humphrey
*Assistant Examiner* — Anjali Ajit Hirani
(74) *Attorney, Agent, or Firm* — Fish & Richardson P.C.

(57) ABSTRACT

A mutant algal strain showing upregulation of mRNA transcripts encoding urea carboxylase, Δ-15-ω3-desaturase and downregulation of mRNA transcripts of gene encoding triacylglycerol lipase is provided herein. The mutant algal strain of the present disclosure is tolerant to low temperature and thus can be grown over a wide temperature range. The strain shows enhanced biomass and fatty acid production and enhanced growth rate and nitrogen metabolism over a wide temperature range of about 10° C. to about 37° C., wherein the enhancement is in comparison to the wild type algal strain. A method of obtaining the mutant algal strain and a method of producing industrially relevant products such as fatty acids from the mutant algal strain also are provided herein.

17 Claims, 4 Drawing Sheets

Specification includes a Sequence Listing.

MUTANT ALGAL STRAIN AND METHODS THEREOF

CROSS-REFERENCE TO RELATED APPLICATIONS

This application claims benefit of priority from Indian Application Serial No. 201921018233, filed on May 7, 2019.

TECHNICAL FIELD

The present disclosure relates to the field of cell biology, microbiology and biotechnology. In particular, the present disclosure relates to a mutant algal strain, where the strain shows upregulation of mRNA transcripts from the genes encoding urea carboxylase and Δ-15-ω3-desaturase, and downregulation of mRNA transcripts from the gene(s) encoding triacylglycerol lipase. The mutant algal strain of the present disclosure is not only tolerant to low temperatures, but also is capable of producing higher levels of polyunsaturated fatty acids (PUFAs), with high growth rates, at such temperatures. The present disclosure further provides a method of obtaining the mutant algal strain and a method of producing industrially relevant products such as fatty acids from the mutant algal strain.

BACKGROUND OF THE DISCLOSURE

Fluctuations of biomass productivity (yield/hector) due to seasonal variation has significant impact on commercialization of technologies that employ photosynthetic microalgae as cell factories. A robust commercialization process requires efficient strains of algae that have high biomass productivities, enhanced nitrogen metabolism, and higher content of omega-3-fatty acids. Eicosapentaenoic acid (EPA, C20:5n3) and docosahexaenoic acid (DHA, C22:6n3) are important ω3 PUFAs, while arachidonic acid (AA, C20:4n6), is a vital ω-6-PUFA. Such PUFAs have numerous nutraceutical and pharmaceutical applications. Microalgae derived PUFAs have superior lipid stability compared with traditional PUFAs, because they are naturally rich in antioxidant carotenoids and vitamins and because lipids are bio encapsulated by the algal cell wall. Therefore, microalgae are some of the most important feed sources in aquaculture due to their nutritional value and their ability to synthesize and accumulate great amounts of ω-3-PUFAs.

The production of lipids from micro algae produced in photobioreactors, fermenters or by pond-farming, depending on the value of the product, is expected to develop rapidly. Among these lipids, ω-3 PUFAs in particular are being studied because of their role in human health, with EPA being considered of immense therapeutic value. For microalgae EPA production to be economically viable, different species that are able to produce more EPA intrinsically and consistently without the need of an additional bioaccumulation while being robust enough to give high productivity are required. Beyond species/strain choice, factors affecting the growth rate and biochemical composition of the cell also must be borne in mind, especially environmental and operating conditions. Natural and wild type strain of algae are known to have high biomass productivities in summer, and significantly lower biomass productivities in winter. The low biomass yield (yield/hector) of algal production strains during winters lowers the average annual productivity of the year. The low temperature stress in winter reduces cellular metabolism and photosynthetic efficiency, and thereby results in poor biomass yield in green plants and photosynthetic microorganisms thus, negatively impacting commercialization metrics.

Algal strains with improved biomass productivity, nitrogen metabolism, and high ω-3-fatty acid content are desired. These features are especially desired at temperatures lower than that at which the strains are usually employed for production purpose, such that strain productivity is maintained over a wide temperature range. Methods to develop such strains and identify the same are therefore required to benefit large scale cultivation of algae for commercialization of products.

SUMMARY OF THE DISCLOSURE

The present disclosure is directed towards a mutant algal strain having enhanced growth characteristics for application in large scale production of lipids and biomass, and methods of production and use thereof.

Accordingly, the present disclosure provides a mutant algal strain in which mRNA transcripts of genes encoding urea carboxylase and Δ-15-ω3-desaturase are upregulated, and mRNA transcripts of the gene encoding triacylglycerol lipase are downregulated as compared to wild type of the algal strain. In particular, the mRNA transcript of the gene encoding urea carboxylase is upregulated by at least about 2 fold, the mRNA transcript of the gene encoding Δ-15-ω3-desaturase gene is upregulated by at least about 5 fold, and the mRNA transcript of the gene encoding triacylglycerol lipase is downregulated by at least about 1.6 fold in the mutant algal strain of the present disclosure, as compared to wild type of the algal strain.

The mutant algal strain of the present disclosure shows about 2 to about 5 fold increase in EPA content during growth phase; about 15% to about 25% increase in total lipid content as dry weight of the cell and about 15% to about 60% increase in volumetric productivity as compared to wild type of the algal strain. Further, the doubling time of the strain also is reduced by about 10% to about 50% as compared to wild type of the algal strain.

The present disclosure further provides a method of obtaining the above-described mutant algal strain, wherein the method includes steps of:

a) subjecting a wild type algal cell population to mutagenesis;

b) followed by subjecting the algal cell population to growth cycle in alternating turbidostat and batch modes to obtain a modified algal cell population; and c) subjecting the modified algal cell population in batch mode to alternating snap dilution and growth cycle;

wherein steps (b) and (c) are conducted in a controlled environment mimicking outdoor environment of temperature ranging from about 10° C. to about 37° C. and light intensity of about 200 μmoles/s/$m^2$ to about 1200 μmoles/s/$m^2$, to obtain a mutant algal cell population comprising the mutant algal strain.

In addition to the above, the present disclosure also relates to an algal cell population produced by the above-described method, wherein the algal cell population shows about 2 fold to about 5 fold increase in EPA content during growth phase as compared to wild type algal cell population.

Further, the present disclosure relates to a method of producing polyunsaturated fatty acid (PUFA), the method include the step of culturing the above-described mutant algal strain and isolating the PUFA. Additionally, the present disclosure also provides a method of producing biomass, the method including the step of culturing the above-described mutant algal strain and isolating the PUFA.

Further provided in the present disclosure, is the use of the mutant algal strain in production of polyunsaturated fatty acids (PUFA) and biomass.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with detailed description below, are incorporated in and form part of the specification, and serve to further illustrate the embodiments and explain various principles and advantages, in accordance with the present disclosure where:

DETAILED DESCRIPTION

Figure 1:
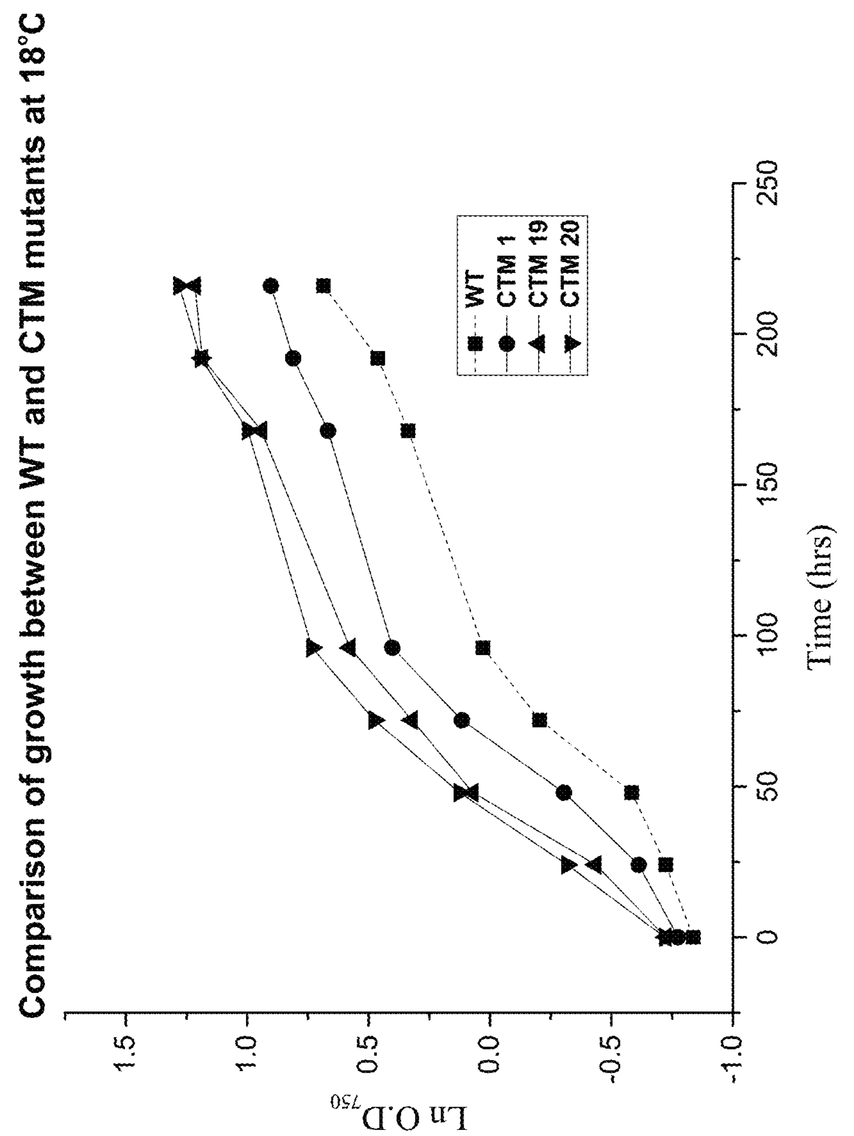
FIG. 1 is a graph plotting growth comparison for a WT *Picochlorum* strain and mutant algal strains of the present disclosure (referred to as CTM1, CTM19 and CTM20) at about 18° C.

In view of the drawbacks associated, and to remedy the need created by the art available in the field of technology related to efficient production of PUFAs by algae, the present disclosure aims to provide a mutant algal strain that is capable of producing enhanced amount of PUFA, total lipids and biomass, while also showing enhanced nitrogen metabolism. An objective of the present disclosure is to provide such a mutant algal strain that is able to show such characteristics over a wide range of temperatures to ensure that the strain is suited for industrial application even at temperatures different from that the usually considered as optimum for the purposes of production.

However, before describing the process in greater detail, it is important to take note of the common terms and phrases that are employed throughout the present disclosure for better understanding of the technology provided herein.

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. As used throughout the present disclosure, ranges are a shorthand for describing each and every value within the range. Any value within the range can be selected as the terminus of the range. The term “about” used in conjunction with values of different parameters defined throughout the specification provides a margin of ±2. The term “and/or” as used in a phrase such as “A and/or B” herein is intended to include “A and B”, “A or B”, “A”, and “B”.

Generally, nomenclatures used in connection with, and techniques of biochemistry, enzymology, molecular and cellular biology, microbiology, genetics and protein/nucleic acid chemistry and hybridization described herein are those well-known and commonly used in the art. To facilitate an understanding of the present disclosure, a number of terms and phrases are defined below.

The terms “algae”, “algal cell”, “algal strain” used interchangeably refer to eukaryotic aquatic organisms belonging to the kingdom Protista, that have the ability to conduct photosynthesis.

The term “strain” as used herein refers to a microorganism (e.g., alga or protist) or a genetic variant or subtype thereof. Unless otherwise specified, the term “strain” in the present disclosure is used in the context of an algal strain.

The phrase “algal cell population” refers to a population comprising at least 2 algal strains.

The phrase “mutant strain” and “mutant algal strain” used interchangeably in the present disclosure refer to an algal strain carrying mutations in the genome leading to upregulation or downregulation of mRNA transcripts of specific genes. The term “mutant strain” as used in the present disclosure excludes natural mutants or naturally occurring algae strains that might show similar characteristics but have not been modified genetically by human manipulation. Mutant strains of the present disclosure have been referred to by the nomenclature CTM-1, CTM-19 and CTM-20—assigned to the strains within the experimental facility. The strains CTM-1, CTM-19 and CTM-20 have been interchangeably referred to by the names Strain 1, Strain 2 and Strain 3, respectively, throughout the disclosure, for ease of reference.

Unless otherwise specified, reference to upregulation or downregulation of features is in comparison to a wild-type algal cell.

The terms “naturally occurring”, “wild-type” and the abbreviation “WT” used interchangeably refer to a form found in nature. For example, a naturally occurring or WT nucleic acid molecule, nucleotide sequence, or protein may be present in, and isolated from, a natural source, and is not intentionally modified by human manipulation. Similarly, a WT organism can be found in natural environment, and such an organism has not been genetically modified by human agency.

The term “biomass” as used herein, refers in general to organic matter produced by a biological cell. The renewable biological resource can include microbial materials (including algal materials) or materials produced biologically. In certain embodiments, the biomass is algal biomass. The algal biomass can be dry, substantially dry, or wet. "Biomass" should be understood to include proteins, lipids, and polysaccharides, whether retained within a biological cell or excreted from a biological cell, in addition to other molecules synthesized by a biological cell.

The term "productivity" refers to the amount of product an organism can produce under defined conditions. Productivity can be measured in grams of dry weight of algal cells. Alternatively, productivity can be measured in terms of the rate of production of a desirable product or product(s) such as lipid (e.g., total lipid or EPA), protein, and/or carbohydrate produced by the organism. The term "volumetric productivity" refers to increase in biomass weight of algae/L/day.

The term "eicosapentaenoic acid" used interchangeably with the abbreviation "EPA", refers to an omega-3 fatty acid polyunsaturated fatty acid with the following connotation C20:5-n3. It is a carboxylic acid with a 20-carbon chain and five cis double bonds; and where the first double bond is located at the third carbon from the omega end.

The term "mRNA transcript" refers to the transcript resulting from transcription of a gene or gene cluster. The upregulation or downregulation of specific mRNA transcripts of the mutant algal strains of the present disclosure has been quantified in terms of the percentage or fold increase or decrease of mRNA encoded by specific cDNA compared to the WT strain, wherein "cDNA" has been used in the same context that is known in the art i.e. DNA synthesized from a single-stranded RNA (e.g., messenger RNA (mRNA) or microRNA) template in a reaction catalysed by the enzyme reverse transcriptase.

The term "gene" means the segment of DNA involved in producing a polypeptide chain. It may include regions preceding and following the coding region (e.g., 5' and 3' untranslated regions, promoters, etc.) as well as intervening sequences (introns) between individual coding segments (exons).

A "turbidostat" is a culture vessel that is capable of monitoring optical density of a cell culture, and of diluting the culture as necessary to maintain a constant optical density despite cell growth within the culture. A reactor may be set at "turbidostat mode".

The term "environmental photobioreactor" referred to by its abbreviation "ePBR" is a bioreactor to cultivate photosynthetic microorganisms while mimicking outdoor conditions that the microorganisms are generally subjected to during outdoor pond cultivation. Reference to temperature ranges maintained in the ePBR in the working examples defines the variable temperature over the cited range, mimicking the variable temperature characteristic of outdoor environments such as outdoor ponds where the strains are to be cultivated during industrial application. A person of skill in the art will be able to appreciate that the temperatures between the ranges referred to in the working examples such as about 12° C. to about 24° C. or about 28° C. to about 30° C. is observed through the course of the day in the 24 hour cycle. All working examples performed under simulated conditions in the ePBR within a defined range of temperature such as about 12° C. to about 24° C. or about 28° C. to about 30° C. may alternatively be performed in the outdoors wherein similar temperature conditions may be observed.

As used herein "pond" means any open body of water, whether naturally occurring or man-made, including but not limited to ponds, canals, trenches, lagoons, channels, or raceways.

Accordingly, to reiterate, the present disclosure relates to a novel algal strain capable of producing higher content of PUFAs. The algal strain of the present disclosure is a mutant algal strain and carries genetic modifications that allow higher production of polyunsaturated fatty acids such as EPA. The mutant algal strain shows upregulation of mRNA transcripts of nitrogen metabolism genes and PUFA synthesis genes, and downregulation of mRNA transcripts of triacylglycerol lipase gene (SDP1) as compared to wild type of the algal strain.

Particularly, the present disclosure relates to a mutant algal strain that shows upregulation of mRNA transcripts of gene encoding urea carboxylase and Δ-15-ω3-desaturase and downregulation of mRNA transcript of gene encoding triacylglycerol lipase, as compared to wild type of the algal strain. The combination of these upregulations and downregulation result in higher production of polyunsaturated fatty acids such as EPA.

The strain which is mutated as per the present disclosure is any algal strain capable of producing PUFA such as EPA. In embodiments of the present disclosure, the algal strain includes but is not limited to *Picochlorum* sp., *Nannochloropsis* sp., *Chlorella* sp., *Chlamydomonas* sp., and *Nannochloris* sp. The algal strain may be sourced from any aquatic source such as but not limiting to oceans, lakes, rivers, ponds (e.g., natural ponds, open culture ponds or greenhouse ponds) and snow.

In a non-limiting embodiment of the present disclosure, the mRNA transcript of the gene encoding urea carboxylase is upregulated by at least about 2 fold, the mRNA transcript of the gene encoding Δ-15-ω3-desaturase gene is upregulated by at least about 5 fold and the mRNA transcript of gene encoding triacylglycerol lipase is downregulated by at least about 1.6 fold in the mutant algal strain as compared to wild type of the algal strain. In some cases, the mRNA transcript of the gene encoding urea carboxylase is upregulated by about 2 to about 9 fold, the mRNA transcript of the gene encoding Δ-15-ω3-desaturase is upregulated by about 5 to about 15 fold and the mRNA transcript of the gene encoding triacylglycerol lipase is downregulated by about 1.6 to about 5 fold as compared to wild type of the algal strain.

In exemplary embodiments of the present disclosure, the mRNA transcript of the gene encoding urea carboxylase is upregulated by about 2, about 3 fold, about 4 fold, about 5 fold, about 6 fold, about 7 fold, about 8 fold or about 9 fold; the mRNA transcript of the gene encoding Δ-15-ω3-desaturase is upregulated by about 5 fold, about 6 fold, about 7 fold, about 8 fold, about 9 fold, about 10 fold, about 11 fold, about 12 fold, about 13 fold, about 14 fold or about 15 fold; and the mRNA transcript of the gene encoding triacylglycerol lipase is downregulated by about 1.6 fold, about 2 fold, about 3 fold, about 4 fold, about 5 fold as compared to wild type of the algal strain.

In some cases, the mRNA transcript of the gene encoding urea carboxylase is upregulated by about 4.2 fold, the mRNA transcript of the gene encoding Δ-15-ω3-desaturase is upregulated by about 10 fold and the mRNA transcript of the gene encoding triacylglycerol lipase is downregulated by about 2.3 fold as compared to wild type of the algal strain.

In addition to the above, the mutant algal strain shows upregulation of mRNA transcript(s) for gene(s) encoding one or more protein(s) selected from a group comprising nitrate reductase, ammonium transporter, nitrite reductase, nitrate transporter, Δ-9-desaturase 3, Δ-9-desaturase 4, Δ-12-desaturase 3 and Δ-12-desaturase 4 as compared to wild type of the algal strain.

In a non-limiting embodiment of the present disclosure, the upregulation of mRNA transcripts for the gene encoding nitrate reductase ranges from about 4 to about 12 fold, for the gene encoding ammonium transporter ranges from about 3 to about 9 fold, for the gene encoding nitrite reductase ranges from about 3 to about 9 fold, for gene encoding nitrate transporter ranges from about 3 to about 9 fold, for the gene encoding Δ-9-desaturase 3 ranges from about 50 to about 120 fold, for the gene encoding Δ-9-desaturase 4 ranges from about 150 to about 250 fold, for the gene encoding Δ-12-desaturase 3 ranges from about 15 to about 45 fold and for the gene encoding Δ-12-desaturase 4 ranges from about 25 to about 60 fold, as compared to wild type of the algal strain.

In exemplary embodiments of the present disclosure, the mRNA transcripts are upregulated for the gene encoding nitrate reductase by about 4 fold, about 6 fold, about 8 fold, about 10 fold or by about 12 fold, for the gene encoding ammonium transporter by about 3, about 5 fold, about 7 fold or 9 fold, for the gene encoding nitrite reductase by about 3 fold, about 5 fold, about 7 fold or about 9 fold, for gene encoding nitrate transporter by about 3, about 5 fold, about 7 fold or about 9 fold, for the gene encoding Δ-9-desaturase 3 ranges by about 50 fold, about 70 fold, about 90 fold, about 100 fold or about 120 fold, for the gene encoding Δ-9-desaturase 4 by about 150 fold, about 170 fold, about 190 fold, about 210 fold, about 220 fold, about 240 fold or 250 fold, for the gene encoding Δ-12-desaturase 3 by about 15 fold, about 20 fold, about 25 fold, about 30 fold, about 35 fold, about 40 fold or about 45 fold and for the gene encoding Δ-12-desaturase 4 by about 25 fold, about 30 fold, about 40 fold, about 50 fold or about 60 fold, as compared to wild type of the algal strain.

As mentioned earlier in the present disclosure, the upregulation or downregulation of specific mRNA transcripts of the mutant algal strains of the present disclosure has been quantified in terms of the percentage or fold increase or decrease of mRNA encoded or represented by specific cDNA compared to the WT strain, wherein "cDNA" has been used in the same context that is known in the art i.e. DNA synthesized from a single-stranded RNA (e.g., messenger RNA (mRNA) or microRNA) template in a reaction catalysed by the enzyme reverse transcriptase. The regulation in levels of mRNA transcripts/corresponding cDNA sequences is assessed by transcriptomics studies using RNA sequence analysis, wherein cDNA from both wild type and the mutant algal strains is sequenced and analysed for fold changes in transcripts using bioinformatics analysis. Accordingly, the mRNA transcript of genes encoding triacylglycerol lipase, nitrate reductase, ammonium transporter, nitrite reductase, nitrate transporter, urea carboxylase, Δ-9-desaturase 3, Δ-9-desaturase 4, Δ-12-desaturase 3, Δ-12-desaturase 4 and Δ-15-ω3-desaturase are represented by cDNA having sequences set forth as SEQ ID Nos. 1 to 11, respectively. Thus, the mutant algal strain of the present disclosure shows upregulation of mRNA transcripts represented by cDNA having sequences set forth as SEQ ID Nos. 2 to 11, respectively and downregulation of mRNA transcript represented by cDNA having sequence set forth as SEQ ID No. 1.

In an embodiment of the present disclosure, the mutant algal strain may be any algal stain having about 30% or less sequence variation in mRNA transcript of genes encoding triacylglycerol lipase, nitrate reductase, ammonium transporter, nitrite reductase, nitrate transporter, urea carboxylase, Δ-9-desaturase 3, Δ-9-desaturase 4, Δ-12-desaturase 3, Δ-12-desaturase 4 and Δ-15-ω3-desaturase represented by cDNA having sequences set forth as SEQ ID Nos. 1 to 11, respectively.

The mutant algal strain of the present disclosure having the above-described regulation in levels of the respective mRNA transcripts is a temperature acclimatized strain. The combination of upregulations and downregulation of the specific mRNA transcripts as described above, makes it feasible to successfully employ the mutant algal strain of the present disclosure in commercial activities over a wide temperature range ranging from about 10° C. to about 37° C., as opposed to the wild type algal strain wherein high productivity is usually limited to high temperatures typical to summer months such as temperatures of above about 24° C. The mutant algal strain of the present disclosure is therefore conferred tolerance to lower temperatures usually characteristic of winter months while retaining productivity at higher temperatures. The mutant algal strain of the present disclosure thus shows favourable productivity and growth characteristics, as described in the below paragraphs, over a wide range of temperatures of about 10° C. to about 37° C. While characteristics that generally are natural to the wild type strain at summer temperatures above about 24° C. are retained in the mutant strain, the mutations to the wild type strain specifically confer the strain with tolerance to temperatures of about 10° C. to 24° C.

The mutant algal strain of the present disclosure therefore shows high productivity, enhanced levels of biomass and enhanced nitrogen metabolism at both winter as well as summer temperatures, wherein, merely for purposes exemplification, without intending to be limited by the present disclosure, while summer temperatures are above about 24° C., winter temperatures range from about 10° C. to about 24° C.

As mentioned previously, while the wild type algal strains show restrained biomass and PUFA production during winter temperatures, the mutant algal strain of the present disclosure is not only able to tolerate such temperatures well, but also shows improved biomass productivity, nitrogen metabolism, and high total lipid, PUFA and ω-3-fatty acid content at such temperatures in addition to retaining natural characteristics of the wild type strain in terms of growth and productivity at summer temperatures.

Therefore, irrespective of the weather conditions, the mutant algal strain of the present disclosure may be cultivated on a small or large scale in indoor or outdoor facilities such as but not limited to reactors and culture ponds.

As mentioned above, one of the important attributes of the mutant algal strain of the present disclosure is its ability to produce higher content of PUFA such as EPA when compared to a WT strain. Accordingly, the mutant algal strain of the present disclosure produces about 3% to about 6% Eicosapentaenoic acid (EPA) of dry weight of the cell, during its growth phase. The yield of EPA is about 2 fold to about 5 fold enhanced as compared to wild type of the algal strain. In alternate terms, the mutant algal strain shows about 2 fold to about 5 fold increase in EPA production as compared to wild type of the algal strain. In an embodiment of the present disclosure, the mutant algal strain shows about 2 fold, about 3 fold, about 4 fold or about 5 fold increase in EPA production as compared to wild type of the algal strain.

Apart from the PUFA, the mutant algal strain also shows higher lipid content when compared to its WT counterpart. Accordingly, the mutant algal strain of the present disclosure shows about 15% to about 25% increase in total lipid content as dry weight of the cell as compared to wild type of the algal strain. This is a significant advantage and likely to positively impact the yield and quality of oil.

In exemplary embodiments of the present disclosure, the mutant algal strain shows about 15%, about 16%, about 17%, about 18%, about 19%, about 20%, about 21%, about 22%, about 23%, about 24% or about 25% increase in total lipid content as dry weight of the cell as compared to wild type of the algal strain.

Further, the regulation in mRNA transcripts leading to the mutant algal strain of the present disclosure also allows for increase in volumetric productivity of the strain by about 15% to about 60% as compared to wild type of the algal strain. Thus, in exemplary embodiments of the present disclosure, the mutant algal strain shows increase in volumetric productivity of the strain by about 15%, about 20%, about 30%, about 40%, about 50% or about 60% as compared to wild type of the algal strain.

Apart from the production related enhancements of the strain, the mutant algae of the present disclosure is also a more efficient strain, with much faster doubling time. Accordingly, the doubling time of the strain of the present disclosure is reduced by about 10% to about 50% as compared to wild type of the algal strain. In exemplary embodiments of the present disclosure, the doubling time of the strain is reduced by about 10%, about 20%, about 30%, about 40% or about 50% as compared to wild type of the algal strain.

The mutant algal strain of the present disclosure also shows enhanced nitrogen metabolism as compared to wild type of the algal strain. The enhanced nitrogen metabolism is evident from upregulation of nitrogen accumulation gene clusters and the enhanced growth of the mutant strains which is primarily due to increased nitrogen consuming ability of the mutant strains since nitrogen is critical for algal growth and photosynthesis.

The mutant algal strain of the present disclosure having the above-described modifications in expression level of mRNA transcripts has been deposited under the provisions of the Budapest Treaty on the International Recognition of the Deposit of Microorganisms for the Purposes of Patent Procedure and the Regulations thereunder (Budapest Treaty). The deposit was made with Culture Collection of Algae and Protozoa (CCAP). The deposit was made with Culture Collection of Algae and Protozoa (CCAP) (SAMS Limited, SAMS, Dunbeg, OBAN, PA37 1QA, Scotland, United Kingdom) on Apr. 24, 2019. The deposited strains have Accession Number CCAP 6079/2 (*Picochlorum* sp. CTM1), Accession Number CCAP 6079/3 (*Picochlorum* sp. CTM19), and Accession Number CCAP 6079/4 (*Picochlorum* sp. CTM20).

While the importance of the present disclosure lies in the mutant strains herein which are more efficient than their wild type counterparts, the aspect of how these strains are obtained or arrived at, is equally critical. The present disclosure thus provides an elaborate method that allows for creation and subsequently, isolation of these mutant strains.

The present disclosure accordingly also relates to a method of obtaining the mutant algal strain described above, which comprises a unique combination of mutagenesis and growth cycle in different modes to obtain mutant algal cell population comprising the mutant algal strain.

More particularly, the method of obtaining the mutant algal strain described above, comprises steps of:

a) subjecting a wild type algal cell population to mutagenesis;
b) followed by subjecting the algal cell population to growth cycle in alternating turbidostat and batch modes to obtain a modified algal cell population; and
c) subjecting the modified algal cell population in batch mode to alternating snap dilution and growth cycle;
  wherein steps (b) and (c) are conducted in a controlled environment mimicking outdoor environment of temperature ranging from about 10° C. to about 37° C. and light intensity ranging from about 200 μmoles/s/m$^2$ to about 1200 μmoles/s/m$^2$, to obtain mutant algal cell population comprising the mutant algal strain.

In another embodiment of the present disclosure, the method of obtaining the mutant algal strain described above consists of steps of:

a) subjecting a wild type algal cell population to mutagenesis;
b) followed by subjecting the algal cell population to growth cycle in alternating turbidostat and batch modes to obtain a modified algal cell population; and
c) subjecting the modified algal cell population in batch mode to alternating snap dilution and growth cycle;
  wherein steps (b) and (c) are conducted in a controlled environment mimicking outdoor environment of temperature ranging from about 10° C. to about 37° C. and light intensity ranging from about 200 μmoles/s/m$^2$ to about 1200 μmoles/s/m$^2$, to obtain mutant algal cell population comprising the mutant algal strain.

The method of the present disclosure is performed by first sourcing and culturing the wild type algal strain including but not limited to *Picochlorum* sp., *Nannochloropsis* sp., *Chlorella* sp., *Chlamydomonas* sp., and *Nannochloris* sp. The wild type algal strain is sourced from any aquatic source such as but not limiting to oceans, lakes, rivers, ponds (for example—natural ponds or open culture ponds) and snow. Once cultured, the wild type algal strain is then subjected to mutagenesis. This mutagenesis may, for example, be a random mutagenesis. Further, the methods by which the wild type algal strain is subjected to mutagenesis, including but not limited to random mutagenesis, are well known to a skilled person and are routinely employed in the art. The random mutagenesis, for example, is affected by exposing the cells to mutagen including but not limited to UV radiation, gamma radiation and chemical agent or any combination thereof. In an embodiment of the present disclosure, the chemical agent includes but is not limited to nitrosoguanidine, DNA base analogs, sodium azide, ROS generating chemicals, metals, intercalating agents like Ethidium bromide (ETBR) and alkylating agents like Ethyl methanesulfonate (EMS) and Methyl methanesulfonate (MMS).

Accordingly, in a non-limiting embodiment of the present disclosure, the wild type algal cell population is subjected to random mutagenesis by exposing the cells to UV radiation of wavelength ranging from about 315 nm to about 400 nm, for a dose ranging from about 300 mJ/m$^2$ to about 2000 mJ/m$^2$, for time period ranging from about 1 minute to about 6 minutes.

When the mutagenesis is random and is caused by exposure to UV radiation, the exposure to UV radiation leads to killing of about 30% to about 90% of the algal cell population. This allows for selection of algal strains that are able to mutate and grow further. Post the mutagenesis, the algal cell population is maintained in darkness for a time period ranging from about 12 hours to about 24 hours, followed by recovery of the cells by subjecting them to about 1% to about 5% $CO_2$, at a temperature ranging from about 25° C. to about 30° C., for a time period ranging for about 5 days to about 15 days.

Post the recovery, the algal cell population is grown in a controlled environment mimicking outdoor environment having temperature ranging from about 10° C. to about 37°

C., $CO_2$ concentration ranging from about 1% to about 5%, pH ranging from about 7 to about 7.5 and photoperiod ranging from about 10 hours to about 16 hours. The culture is maintained at a depth of about 10 cm to about 20 cm and subjected to mixing at 200 rpm to 800 rpm. In an embodiment, the ePBR is maintained under simulated sinosoidal light intensity (i.e. 12 hr Light/12 hr Dark with peak intensity of about 1200 μmoles/s/$m^2$ to about 100 μmoles/s/$m^2$ during the simulated day time.

In a non-limiting embodiment of the present disclosure, the controlled environment is maintained in a reactor such as but not limiting to an environmental photobioreactor. In another non-limiting embodiment, the algal cell population is grown in growth medium selected from a group comprising nutrient media such as Urea phosphoric (UPA) medium, BG-11 medium, F/2 medium combined with nitrate, Bold's Basal Medium (BBM) and artificial sea water medium or any combination thereof. In some cases, the growth medium is UPA medium, wherein the medium comprises sea water having salinity ranging from about 2% to about 4%, urea at a concentration ranging from about 25 ppm to about 200 ppm, $H_3PO_4$ at a concentration ranging from about 0.5 ppm to about 3 ppm and trace element mix at a concentration ranging from about 1 ml/L to about 2 ml/L, wherein pH of the medium is maintained about 6.8 to about 8. In an embodiment of the present disclosure, the UPA medium comprises sea water having salinity ranging from about 0.34 M to about 0.68 M, urea at a concentration ranging from about 0.41 mM to about 3.33 mM, $H_3PO_4$ at a concentration ranging from about 0.05 mM to about 0.31 mM and trace element mix at a concentration ranging from about 1 ml/L to about 2 ml/L.

Growth of the algal cell population is allowed to continue till the cell count multiplies by about 4 to about 6 fold as compared to the initial population. Subsequently, the reactor is adjusted to turbidostat mode for about 3 to about 4 days followed by batch mode for about 6 days to about 8 days to obtain a modified algal cell population. The growth cycle in alternating turbidostat and batch modes is repeated till the modified algal cell population shows about 2 fold to about 5 fold increase in PUFA content, such as that of EPA, as compared to the wild type algal cell population.

In a non-limiting embodiment, upon recovering after the exposure to UV radiation, for an ePBR having capacity ranging from about 100 ml to about 500 ml, the cell count is allowed to reach about $1\times10^9$ cells per ml to about $3\times10^9$ cells per ml. For example, for an ePBR having capacity ranging from about 250 ml to about 500 ml, the cell count is allowed to reach about $1.5\times10^9$ cells per ml. At this stage, the ePBR is washed by increasing flow rate by about 50% to about 80% and set to turbidostat mode to reduce cell count to about $1\times10^8$ cells per ml to about $5\times10^8$ cells per ml. Again, for example, for an ePBR having capacity ranging from about 250 ml to about 500 ml, the turbidostat is set to reduce the cell count to about $2\times10^8$ cells per ml.

After about 3 to about 4 days of maintaining the algal population in turbidostat mode, the reactor is set to batch mode till a cell count close to the initial cell count is re-achieved, i.e., cell count which was before setting the culture to turbidostat mode. For example, making the culture again reach cell count of about $1\times10^9$ cells per ml to about $3\times10^9$ cells per ml for an ePBR having capacity ranging from about 250 ml to about 500 ml.

The alternation between turbidostat and batch modes of culture is repeated till the modified algal cell population shows about 2 fold to about 5 fold increase in PUFA content, such as EPA, as compared to the wild type algal cell population. Typically, the alternation between turbidostat and batch modes of culture is repeated for about 20 to about 25 times.

In embodiments of the present disclosure, a total of about 250 days to about 280 days of alternate turbidostat and batch mode operation of the culture yields an algal cell population showing about 2 fold to about 5 fold increase in EPA content as compared to the wild type algal cell population.

In an alternative embodiment of the present disclosure, the order of the turbidostat and batch modes of culture may be reversed wherein the culture is first grown in batch mode and then switched to turbidostat mode. Therefore, the culture may be alternated between turbidostat and batch modes in any order, to prepare the modified algal cell population. Cell growth in turbidostat mode is performed to establish a homogenous population in exponential phase and generate biomass whereas growth in batch mode ensures that EPA production is maximum during early stationary/late exponential phase.

As mentioned previously, the modified algal cell population shows EPA content of about 3% to about 6% EPA of dry weight of the cell, during growth phase. However, the high EPA content producing modified algal cell population at this stage has a doubling time of about 6 days.

Since higher growth rates are desired along with continued high productivity of PUFA such as EPA, the present disclosure provides further process steps to improve the doubling time, with maintenance of high PUFA content. To achieve the same, the modified algal cell population is further subjected to repeated snap dilution and growth to reduce doubling time, while maintaining the PUFA content, including that of EPA. The repeated snap dilutions enable elimination of slow growing cells such that only fast growing populations that are dividing actively get enriched.

Accordingly, once the higher content of PUFA, including EPA is achieved by the alternation of turbidostat and batch modes as described above, the algal cell population maintained in batch mode of operation is then subjected to snap dilution. The modified algal cell population maintained in batch mode of operation is subjected to snap dilution every about 4 days to about 5 days of growth in batch mode, repeating the dilution-growth cycle for about 70 to about 120 generations to obtain faster growing mutant algal cell population. In a non-limiting embodiment of the present disclosure, the dilution-growth cycle is repeated till doubling time of the modified algal cell population is reduced by at least about half. In another embodiment of the present disclosure, the dilution-growth cycle is repeated till doubling time of the mutant algal cell population is reduced to about 4 days to about 3 days.

The mutant algal cell population comprises a pool of mutant algal strains. The pool of mutant algal strains shows characteristics of improved PUFA, including EPA, content and reduced doubling time.

In an embodiment of the present disclosure, the order of steps of the above described method is modified, wherein step (c) is performed before step (b) such that the algal cell population subjected to mutagenesis is first subjected to growth under controlled conditions to generate an algal cell population having reduced doubling time followed by further growth in controlled conditions to generate a high EPA content producing algal cell population. Thus, regardless of the order of the steps, it is the combination of growth conditions along with mutagenesis that allows for mutated algal strain of the present disclosure which showcases simultaneous advantages of high and quick growth and efficient PUFA production, including production of high EPA content.

As desired, post generation of the mutant algal cell population, the best performing individual strains are isolated in pure culture from the pool of mutant algal strains. The mutant algal cell population is subjected to sorting to identify and isolate the best performing strains. In exemplary embodiments, the sorting is performed by methods such as but not limiting to Fluorescence Activated Cell Sorting (FACS). In a non-limiting embodiment of the present disclosure, the parameter for FACS sorting is forward-angle light scatter (FSC) and side-angle scatter (SSC) measurements concurrently to sort out cells with a size range of about 2 μ to about 3 μ. Further, chlorophyll fluorescence of algae is relied upon to specifically sort live algae cells.

The sorted cells are further subjected to screening by dispersing into 96-well plate for further screening and isolation of the best performing strains. The 96 well plates have liquid media similar to that used for their growth, such as Urea-phosphoric (UPA) medium. In an embodiment of the present disclosure, at least 50% of the best performing strains revived on the 96-well plate upon exposure to the liquid growth medium. The revived individual mutant cells are checked for growth at a low temperature of about 10° C. to about 24° C. to confirm enhanced growth under selection conditions (i.e., low temperature of about 10° C. to about 24° C.). This growth screening at a low temperature of about 10° C. to about 24° C. is repeated for about 100 mutants and finally best performing mutants showing stable better growth phenotype are selected. The relatively low temperatures of about 10° C. to about 24° C. employed in the screening and isolation steps are temperatures that the strains are not usually tolerant to. The individual strains are further confirmed for their high PUFA content, such as that of EPA, along with high growth rates by further growth for example in kuhner flasks, at the relatively low temperature. The technique overcomes reliance on growth on solid media, thus extending application to various other natural strains that show poor or no growth on solid media.

In a further embodiment of the present disclosure, growth of the isolated mutated algal strains is evaluated and further confirmed at temperatures ranging from about 10° C. to about 37° C., under real or simulated environmental conditions. In one embodiment, the further evaluation of growth is performed at relatively low temperatures of about 10° C. to about 24° C., to which the wild type strains are not usually tolerant.

Accordingly, as expected, the isolated mutant algal strain obtained from the above described method produces about 3% to about 6% PUFA, such as EPA, as dry weight of the cell, during growth phase. Further, the isolated mutant algal strain also shows about 15% to about 25% increase in total lipid content as dry weight of the cell; about 15% to about 60% increase in volumetric productivity; and about 10% to about 50% decrease in doubling time as compared to wild type of the algal strain. Not intending to be limited by the present disclosure, total lipids can be measured as Fatty acid methyl esters (FAME) using Gas Chromatography after transesterification of lipids using low sample volume. Fatty acids are present in cis and trans configuration. The differences between cis isomer FAMEs and trans-isomer FAMEs of the same carbon length and degree of unsaturation are very small. Therefore, estimation of FAMEs requires very efficient capillary GC columns with highly polar phases.

In an embodiment, the present disclosure provides a method of upregulating mRNA transcripts of gene encoding one or more protein(s) selected from a group comprising urea carboxylase, Δ-15-ω3-desaturase nitrate reductase, ammonium transporter, nitrite reductase, nitrate transporter, Δ-9-desaturase 3, Δ-9-desaturase 4, Δ-12-desaturase 3 and Δ-12-desaturase 4 and downregulating mRNA transcript of gene encoding triacylglycerol lipase in an algal strain to produce a mutant algal strain, comprising steps of:

a) subjecting a wild type algal cell population to mutagenesis;
b) followed by subjecting the algal cell population to growth cycle in alternating turbidostat and batch modes to obtain a modified algal cell population; and
c) subjecting the modified algal cell population in batch mode to alternating snap dilution and growth cycle;
wherein steps (b) and (c) are conducted in a controlled environment mimicking outdoor environment of temperature ranging from about 10° C. to about 37° C. and light intensity ranging from about 200 μmoles/s/m$^2$ to about 1200 μmoles/s/m$^2$, to obtain mutant algal cell population comprising the mutant algal strain.

Without intending to be limited by the scope of the present disclosure, it is a common practice in the art for mRNA regulation to be quantified in terms of regulation of corresponding cDNA sequences in transcriptomics studies. In an embodiment, the upregulation and downregulation of mRNA transcripts is estimated by measuring the level of corresponding cDNA sequences, wherein the mRNA transcript of genes encoding triacylglycerol lipase, nitrate reductase, ammonium transporter, nitrite reductase, nitrate transporter, urea carboxylase, Δ-9-desaturase 3, Δ-9-desaturase 4, Δ-12-desaturase 3, Δ-12-desaturase 4 and Δ-15-ω3-desaturase are encoded by cDNA having sequences set forth as SEQ ID Nos. 1 to 11, respectively. The fold regulation of mRNA transcripts is determined by transciptomics studies that show similar increase in corresponding cDNA sequences of the mRNA transcripts.

The mutant algal cell having the regulation of mRNA transcripts obtained by isolation from the algal cell population derived from the above defined method shows about 2 fold to about 5 fold increase in PUFA content, such as the content of EPA, during growth phase as compared to the wild type of the algal cell, doubling time reduced by about 10% to about 50% and volumetric productivity increased by about 15% to about 60% as compared to wild type of the algal strain.

As mentioned previously, the isolated mutant algal strains obtained by the method of the present disclosure have been deposited under the provisions of the Budapest Treaty on the International Recognition of the Deposit of Microorganisms for the Purposes of Patent Procedure and the Regulations thereunder (Budapest Treaty).

The present disclosure further provides an algal cell population produced by the above described method, wherein the algal cell population shows about 3 fold to about 5 fold increase in PUFA content, such as the content of EPA, during growth phase as compared to wild type algal cell population. In an embodiment of the present disclosure, the algal strain in the population has doubling time reduced by about 10% to about 50% and volumetric productivity increased by about 15% to about 60% as compared to wild type of the algal strain.

As mentioned previously, one of the important objectives of the present disclosure is to provide mutant algal population and/or strain that is capable of producing high levels of PUFA with reduced doubling time. Thus, the present disclosure also relates to production of PUFA by the mutant algal population and/or strain of the present disclosure. The method of producing polyunsaturated fatty acid (PUFA), therefore comprises the step of culturing the mutant algal strain or a population thereof of the present disclosure, to produce the PUFA. As mentioned above, briefly reiterating, this involves employing a WT algal strain or population thereof, and subjecting it to the process of mutagenesis, followed by growth cycles in different modes including turbidostat mode and batch mode, followed by alternating snap dilution and growth in batch mode to obtain mutant algal cell strain and/or population of the present disclosure, which is capable of producing high content of PUFA such as EPA, higher total lipid content and higher biomass with reduced doubling time as compared to the WT strain or population thereof.

In a further non-limiting embodiment of the present disclosure, the method of producing PUFA from the mutant algal strain further comprises step of extracting total lipids from the culture followed by isolation and identification of PUFA. In an embodiment, the PUFA is isolated by solvent based method and analysed by Gas Chromatography (GC) after transesterification. In another embodiment, yield of the PUFA is about 2 fold to about 5 fold higher as compared to the method employing a wild type of the algal strain.

In embodiments of the present disclosure, the PUFA is EPA.

Thus, in applications where the PUFA such as EPA is essential to be produced, the mutant algal strain of the present disclosure or a population thereof can be used. The present disclosure thus further relates to use of the mutant algal strain in the production of the polyunsaturated fatty acids (PUFAs) including EPA.

Another key advantage of the mutant algal strain of the present disclosure is the increased volumetric productivity and hence, increased yield of biomass produced by the strain. The present disclosure therefore also provides a method of producing biomass, the method including the step of culturing the mutant algal strain of the present disclosure to produce the biomass. In an embodiment, the yield of the biomass employing the mutant algal strain of the present disclosure is about 15% to about 60% higher as compared to the method employing a wild type of the algal strain.

The present disclosure further relates to use of the mutant algal strain in the production of biomass from the culture of the mutant algal strain.

In one of the embodiments of the present disclosure, the biomass is rich in total lipids and fatty acids.

Taken together, the present disclosure provides a mutant algal strain having differentially regulated mRNA transcripts encoding genes and gene-clusters which have a role to play in temperature tolerance, biomass and EPA production.

In an exemplary embodiment, the present disclosure relates to a mutant algal strain, wherein mRNA transcript of the gene encoding urea carboxylase is upregulated by about 4.2 fold, the mRNA transcript of the gene encoding Δ-15-ω3-desaturase is upregulated by about 10 fold and the mRNA transcript of the gene encoding triacylglycerol lipase is downregulated by about 2.3 fold as compared to wild type of the algal strain. The strain has been deposited with CCAP. The strain is obtained by a method comprising steps of:

a) subjecting a wild type algal cell population to mutagenesis;
b) followed by subjecting the algal cell population to growth cycle in alternating turbidostat and batch modes to obtain a modified algal cell population; and
c) subjecting the modified algal cell population in batch mode to alternating snap dilution and growth cycle;

wherein steps (b) and (c) are conducted in a controlled environment mimicking outdoor environment of temperature ranging from about 10° C. to about 24° C. and light intensity ranging from about 200 μmoles/s/$m^2$ to about 1200 μmoles/s/$m^2$, to obtain mutant algal cell population comprising the mutant algal strain.

The strain obtained by identification and isolation from the algal cell population obtained, based on best performance in terms of growth and productivity at a temperature ranging from about 10° C. to about 24° C., shows about 2 fold to about 5 fold increase in PUFA content, such as the content of EPA, during growth phase as compared to wild type of the algal cell. In an embodiment of the present disclosure, the algal strain has doubling time reduced by about 10% to about 50% and volumetric productivity increased by about 15% to about 60% as compared to wild type of the algal strain.

The present disclosure provides for an improved method to obtain and isolate mutants with improved growth and nitrogen metabolism, and improved ω-3-fatty acid content, total lipid and biomass at low temperature. The enhanced production of EPA provided by the mutant algal strain is of particular importance in terms of industrial applicability. This is achieved by the differential regulation of the mRNA transcripts described in the above paragraphs, which is responsible for generation of low temperature tolerant, high lipid, high biomass and enhanced EPA producing phenotype. The mutant algal strain of the present disclosure also shows reduced doubling time and enhanced biomass productivity over a wide temperature range of about 10° C. to about 37° C., as compared to the wild type algal strain, in addition to production of high EPA and lipid content.

Additional embodiments and features of the present disclosure will be apparent to one of ordinary skill in art based upon description provided herein. The embodiments herein provide various features and advantageous details thereof in the description. Descriptions of well-known/conventional methods and techniques are omitted so as to not unnecessarily obscure the embodiments herein. Further, the disclosure herein provides for examples illustrating the above described embodiments, and in order to illustrate the embodiments of the present disclosure, certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Materials and Methods

The algal cells employed in the present invention were *Picochlorum* sp. from the Applicant's strain collection in its research facility. The *Picochlorum* strain was collected from Maharashtra coast at Karanja (N18.844663, E72.946313).

The culture medium employed for culturing of the algal cells was UPA medium having the following composition:

TABLE 1

| Urea-phosphoric media (UPA) + 1X f/2 trace metal mix | | |
|---|---|---|
| Media components | Final Concentration | Amount added/L |
| Sea water (~4% salinity) | 900 ml | — |
| Urea | 3.33 mM | 200 mg |
| $H_3PO_4$ | 0.31 mM | 0.31 ml from 1M stock |
| F/2-Trace element mix | $FeCl_3$ $6H_2O$ (23.4 μM), $Na_2EDTA$ $2H_2O$ (23.4 μM), $CuSO_4$ $5H_2O$ (78.6 nM), $Na_2MoO_4$ $2H_2O$ (52.0 nM), ZnSO4 $7H_2O$ (0.153 μM), $CoCl_2$ $6H_2O$ (84.0 nM) and $MnCl_2$ $4H_2O$ (1.82 μM) | 1 ml/L (500 X stock) |

pH was adjusted to 7.5, sea water was added to make up volume to 1L and the medium was autoclaved.

Example 1: Generation of High EPA Content Producing Mutant Algal Cells

About 10 ml culture of *Picochlorum* having $1\times10^8$ cells/ml was subjected to random mutagenesis by exposing to UV radiation of wavelength about 340 nm for about 2 minutes at a dose of about 600 mJ/$m^2$. After the UV exposure, the cells were kept in dark overnight and then recovered in about 2% $CO_2$, at a temperature of about 30° C. and under light having intensity of about 200 μMoles/s/$m^2$ for about 2 weeks.

A population of about $5\times10^7$ cells/ml recovered cells was inoculated in about 500 ml of UPA medium in an environmental-photobioreactor (e-PBR—Phenometrics, USA). The ePBR was maintained at a temperature of about 18° C.±2° C., under simulated sinosoidal light intensity (12 hr Light/12 hr Day) with peak intensity of about 1200 μmoles/s/$m^2$ during the simulated day time. The culture was maintained at a depth of about 20 cm within mixing at about 400 rpm. The pH was maintained at about 7.5±2 by bubbling $CO_2$.

Growth of the culture was monitored by taking cell counts using Flow cytometer (BD accuri). Once cell count of about $1.5\times10^9$ cells per ml was achieved, the reactor was washed by diluting with fresh media up to 80% of the total volume and the reactor was set at turbidostat mode to maintain cell count of about $2\times10^8$ cells/ml. The population of $2\times10^8$ cells/ml was maintained for about 3 to 4 days. The reactor was then set at batch mode till the culture reached a cell count of $3\times10^9$ cells per ml.

The growth cycles in alternating turbidostat and batch modes were repeated till the population showed EPA content of about 4% to 6% as dry weight of the cell. The high EPA content producing population accordingly comprises modified algal cell strain(s), modified for high EPA production.

Example 2: Generation of High Growth Rate and High EPA Content Producing Mutant Algal Cells The high EPA content producing culture of Example 1 was subjected to further growth wherein batch mode of operation was subjected to snap dilution to about $2.5\times10^8$ cells/ml in every about 4 days. This cycle was repeated for about 70 generations and during this repeated growth, the growth rate of the population was continuously monitored. The doubling time of the population was reduced to about 3 days at the end of the alternation snap dilation and growth cycles, as compared to about 6 days at the end of Example 1. The EPA levels were verified to ensure they have not changed from the initial about 4% to 6% of dry weight of the cells achieved at the end of Example 1.

Example 3: Identification and Isolation of Mutants

The population of high EPA content producing mutant algal cells also having high growth rate, obtained at the end of Example 2 was subjected to sorting by FACS (BD Arya) to isolate individual mutants. Parameter for FACS sorting used was forward-angle light scatter (FSC) and side-angle scatter (SSC) measurements concurrently to sort out cells with a size range of 2-3 μM. Further, the chlorophyll fluorescence of algae was captured by signal in FL3 detector (fluorescence channel 3-488-nm laser excitation, 670 LP (long pass) filter emission) to specifically sort live algae cells.

The cells sorted by FACS were dispersed in 96 well plates having 100 μl UPA liquid media. The 96 well plates were kept at about 18° C. and about 50% of the sorted cells were revived and checked for growth at 18° C. These individual mutants were further checked for growth at 18° C. in triplicates in kuhner shaker and around 100 mutants were shortlisted based on their improved growth and consistent EPA content at 18° C. From the 100 mutants identified in Example 3, further selection of the best performing strains (3 strains CTM1, CTM19 and CTM20, hereinafter referred to as Strain 1, Strain 2 and Strain 3) was performed based on their repeated best growth performance during growth screening at 18° C. in the e-PBR.

Example 4: Culturing of the Mutant Algal Strain

The mutant algal strains—(Strain 1, Strain 2 or Strain 3) were inoculated at about 0.45 OD (750 nm) in separate Phenometrics Photo-Bioreactors (PBRs) in UPA medium. The volume of the culture was maintained at about 500 mL and depth was maintained at about 20 cm. The light condition was 12 hour light and 12 hour dark sinusoidal cycle with the peak intensity of about 1200 μE at about 14 hours. The temperature in 3 separate ePBRs for each strain was maintained at about 18° C., about 12° C. to 24° C. (variable temperature mimicking outdoor pond conditions) and about 28° C. to 30° C. (variable temperature) and the pH was maintained at about 7.5±0.5 by $CO_2$ sparging.

Alternatively, experiments carried out over variable temperatures of about 12° C. to 24° C. and about 28° C. to 30° C. were facilitated by inoculating the strain in outdoor ponds wherein the temperatures within the defined ranges existed through the course of the day or in greenhouse ponds.

Example 5: Analysis of Growth Rates and Volumetric Productivities of the 3 Isolated Algal Mutant Strains Growth rates of the three mutants in the ePBR was analysed at temperatures of about 18° C., about 12° C. to 24° C. and about 28° C. to 30° C.

Further, volumetric productivity in terms of increase in biomass was analysed at temperatures of about 18° C., about 12° C. to 24° C. and about 28° C. to 30° C.

The results of the analysis are provided in Tables 2 and 3.

TABLE 2

The doubling time (DT) and volumetric productivities (VP) of the mutants under different growth conditions in e-PBRs compared to wild type *Picochlorum* strain

| | Growth at 18° C. and reduction in doubling time (DT) | | Growth at 18° C. and improvement in volumetric productivity (VP) | | Growth at 12° C.-24° C. and reduction in doubling time (DT) | | Growth at 12° C.-24° C. and improvement in volumetric productivity (VP) | |
|---|---|---|---|---|---|---|---|---|
| Strain | DT | % reduction | VP mg/l/day | % Improvement | DT | % reduction | VP mg/l/day | % Improvement |
| Wild type | 124.89 ± 8.32 | — | 38.81 ± 12.56 | — | 100.84 ± 4.36 | — | 50.97 ± 6.86 | — |
| Strain 1 | 81.47 ± 5.74 | 35 | 54.76 ± 9.25 | 41 | 80.39 ± 6.81 | 20 | 64.02 ± 8.93 | 26 |
| Strain 2 | 76.56 ± 6.29 | 39 | 58.24 ± 7.48 | 48 | 77.13 ± 3.54 | 24 | 67.55 ± 9.41 | 32 |
| Strain 3 | 73.42 ± 5.17 | 41 | 62.83 ± 10.23 | 61 | 73.27 ± 7.14 | 27 | 71.39 ± 11.66 | 40 |

TABLE 3

The doubling time (DT) and volumetric productivities (VP) of the mutants grown at about 28° C.-30° C. in e-PBR compared to wild type *Picochlorum* strain

| | Growth and DT at 28° C.-30° C. | | VP at 28° C.-30° C. | |
|---|---|---|---|---|
| Strain | DT | % reduction | VP mg/l/day | % Improvement |
| Wild type | 70.22 ± 3.16 | — | 90.33 ± 4.86 | — |
| Strain 1 | 62.39 ± 2.41 | 11 | 105.52 ± 6.23 | 17 |
| Strain 2 | 60.83 ± 3.54 | 13 | 111.55 ± 8.71 | 23 |
| Strain 3 | 56.57 ± 4.18 | 20 | 116.77 ± 10.36 | 29 |

Figure 2:
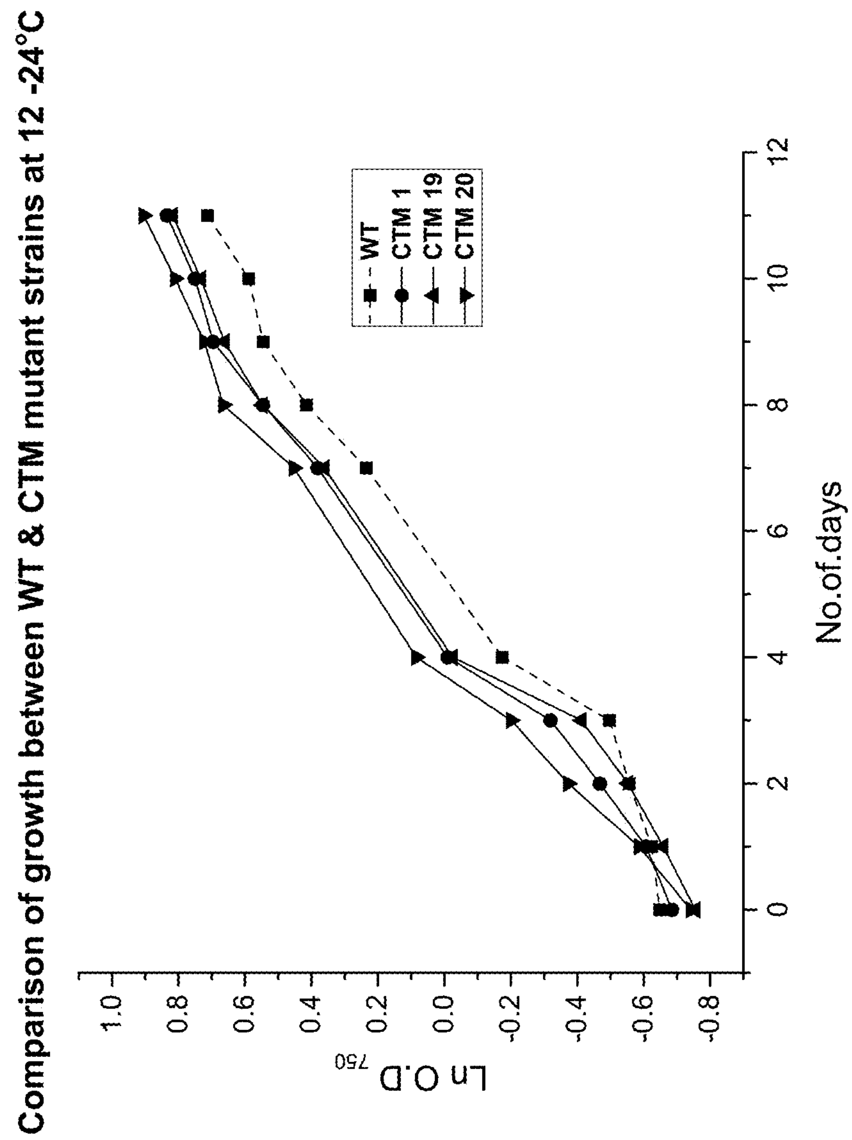
FIG. 2 is a graph plotting growth comparison for a WT *Picochlorum* strain and mutant algal strains of the present disclosure (referred to as CTM1, CTM19 and CTM20) at about 12° C. to 24° C.
Figure 3:
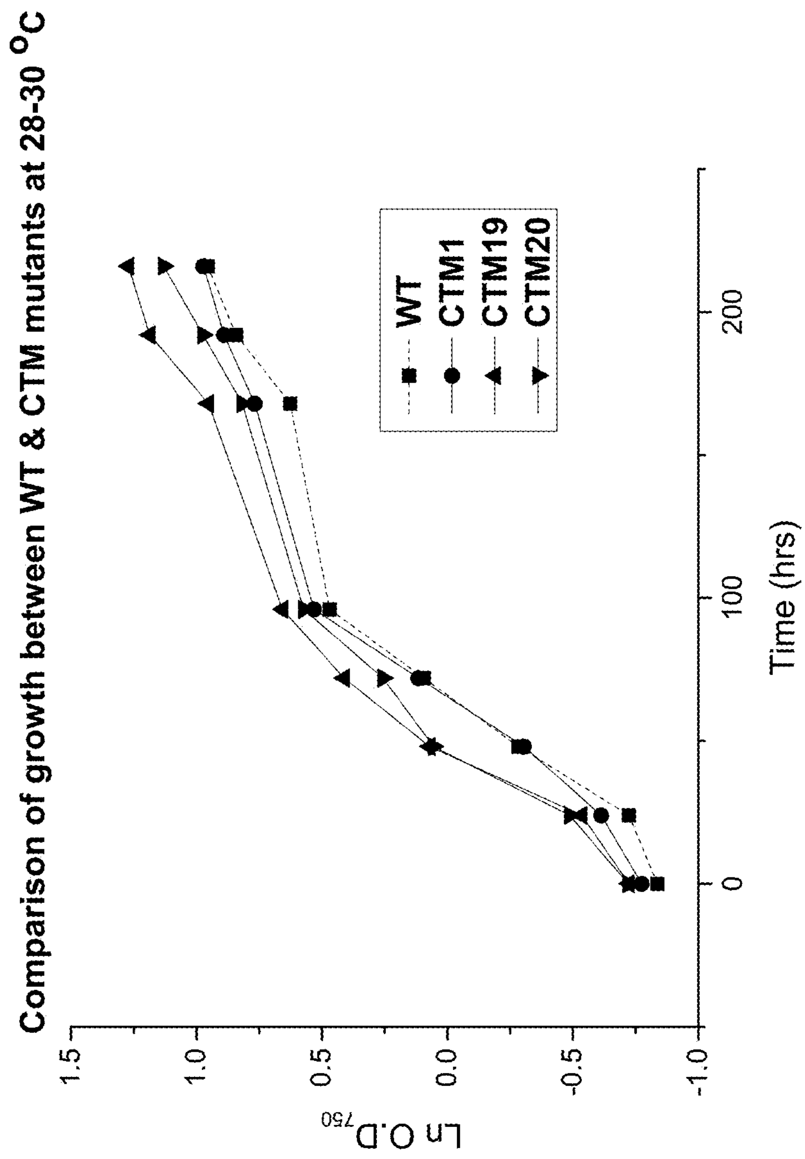
FIG. 3 is a graph plotting growth comparison for a WT *Picochlorum* strain and mutant algal strains of the present disclosure (referred to as CTM1, CTM19 and CTM20) at about 28° C. to 30° C.

The three mutants—Strain 1, Strain 2 and Strain 3—displayed about 35%-41% decrease in doubling time and about 41%-61% increase in volumetric productivity (mg/l/day) as compared to the WT *Picochlorum* strain at about 18° C. (Table 3, FIG. 1); about 20%-27% decrease in doubling time and about 26%-40% increase in volumetric productivity under simulated winter conditions of about 12° C. to 24° C. (Table 3, FIG. 2) and about 11%-20% decrease in doubling time and about 17%-29% increase in volumetric productivity under simulated conditions of about 28° C. to 30° C. (Table 3, FIG. 3).

Example 6: Lipid Estimation

The total lipid amount produced by the cultures of the three algal mutant strains of Example 4 was estimated using minimum biomass by employing a modified Bligh and Dyer method*. The estimation could also be made by other techniques commonly practiced in the art.

The results are shown in Tables 4, 5 and 6.

TABLE 4

Total and neutral lipid as % of biomass for WT *Picochlorum* strain and mutants grown at about 18° C.

| Strain | Total Lipid (%) | Neutral Lipid (%) |
|---|---|---|
| WT | 25.6 ± 0.61 | 11.72 ± 0.19 |
| Strain 1 | 29.2 ± 0.83 | 13.8 ± 0.56 |
| Strain 2 | 31.36 ± 0.48 | 14.2 ± 0.41 |
| Strain 3 | 30.8 ± 0.33 | 13.5 ± 0.71 |

TABLE 5

Total and neutral lipid as % of biomass for WT *Picochlorum* strain and mutants grown at about 12° C.-24° C.

| Strain | Total Lipid (%) | Neutral Lipid (%) |
|---|---|---|
| WT | 21.34 ± 0.71 | 10.54 ± 0.17 |
| Strain 1 | 24.76 ± 0.42 | 12.32 ± 0.11 |
| Strain 2 | 25.81 ± 0.33 | 12.97 ± 0.54 |
| Strain 3 | 26.85 ± 0.29 | 13.22 ± 0.69 |

TABLE 6

Total and neutral lipid as % of biomass for WT *Picochlorum* strain and mutants grown at about 28° C.-30° C.

| Strain | Total Lipid (%) | Neutral Lipid (%) |
|---|---|---|
| WT | 19.6 ± 0.64 | 9.82 ± 0.15 |
| Strain 1 | 22.8 ± 1.13 | 11.1 ± 0.33 |
| Strain 2 | 23.56 ± 0.45 | 11.2 ± 0.11 |
| Strain 3 | 23.1 ± 0.69 | 10.8 ± 0.21 |

Figure 4:
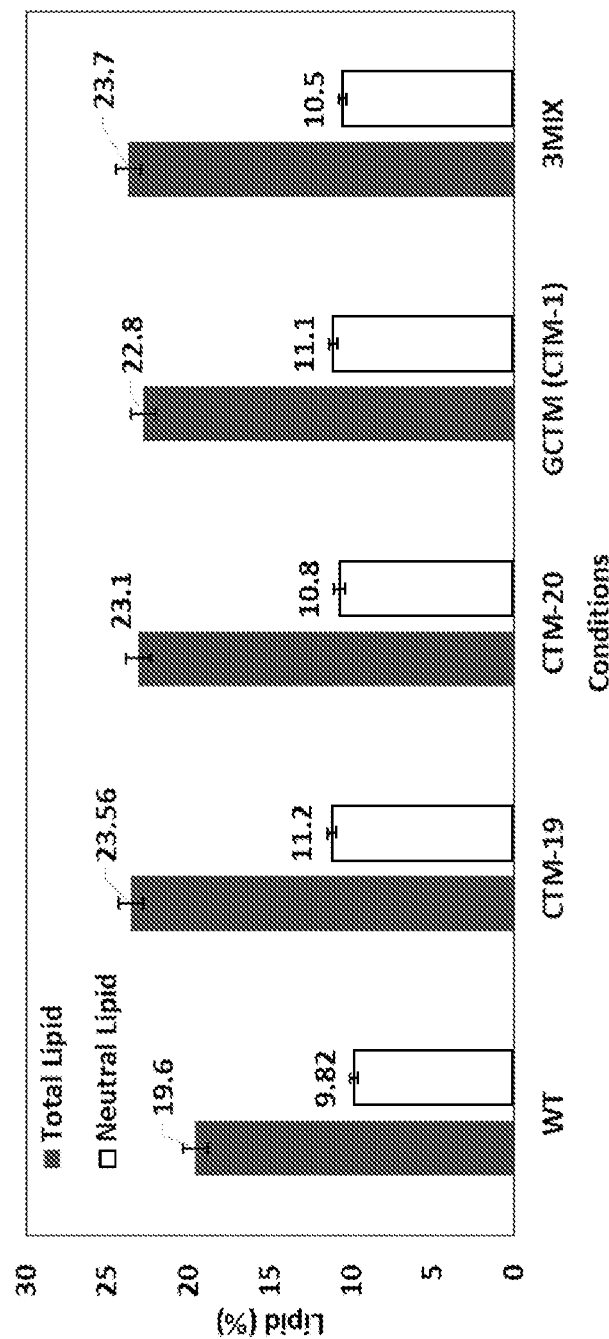
FIG. 4 is a graph plotting the total and neutral lipid content of WT *Picochlorum* strain mutant algal strains of the present disclosure (referred to as CTM1, CTM19 and CTM20) grown individually in UPA media at about 28° C. to 30° C.

The total lipid produced by the three algal mutant strains was found to be increased by about 14%-22% at 18° C., by about 16%-25% at about 12° C. to 24° C. and by about 16%-20% at about 28° C. to 30° C. when compared to wild type *Picochlorum* strain in growth or exponential phase (FIG. 4 shows the total lipid levels at about 28° C. to 30° C.).

Example 7: Determination of EPA Content Produced by the 3 Isolated Algal Mutant Strains EPA content produced by the cultures of the three algal mutant strains of Example 4 was determined by estimating EPA methyl esters content (by FAME analysis*) employing the highly polar SP-2560 column specifically designed for the separation of geometric-positional (cis/trans) isomers of FAMEs with nitrogen as mobile phase.

Tables 7, 8 and 9 provide results for estimation of EPA content at temperatures of about 18° C., about 12° C. to 24° C. and about 28° C. to 30° C., respectively.

TABLE 7

EPA content analysis by GC of the WT *Picochlorum* strain and mutant Strains 1-3 grown in UPA media at about 18° C.
EPA as % dry weight of *Picochlorum* strain and mutant strains 1-3 grown at about 18° C.

| | WT | Strain 1 | Strain 2 | Strain 3 |
|---|---|---|---|---|
| methyl cis 5,8,11,14,17-eicosapentaenoate (C20:5n3) EPA | 165 ± 0.51 | 476 ± 0.69 | 583 ± 0.24 | 396 ± 0.36 |

TABLE 8

EPA content analysis by GC of the WT *Picochlorum* strain and CTM1, CTM19 and CTM20 mutants grown in UPA media about 12° C.-24° C. EPA as % dry weight of *Picochlorum* strain and mutant strains 1-3 grown at about 12° C.-24° C.

| | WT | CTM1 | CTM19 | CTM20 |
|---|---|---|---|---|
| methyl cis 5,8,11,14,17-eicosapentaenoate (C20:5n3) EPA | 1.13 ± 0.24 | 3.25 ± 0.69 | 4.17 ± 0.54 | 3.47 ± 0.31 |

TABLE 9

EPA content analysis by GC of the *Picochlorum* -WT strain and the three mutant algal strains grown in UPA media at about 28° C.-30° C. EPA as % dry weight biomass of RIL601 and mutant Strains 1-3 grown at about 28° C.-30° C.

| | WT | Strain 1 | Strain 2 | Strain 3 |
|---|---|---|---|---|
| methyl cis 5,8,11,14,17-eicosapentaenoate (C20:5n3) EPA | 1.4 ± 0.47 | 3.9 ± 0.34 | 4.1 ± 0.58 | 3.1 ± 0.24 |

The total fatty acid analysis of the three algal mutant strains (Strain 1, Strain 2 and Strain 3) showed production of EPA content of about 4.76%, about 5.83% and about 3.96% as dry weight of the cell respectively in growth (exponential phase) at about 18° C. (Table 7). The EPA content is about 188% (2.9 fold), about 253% (3.5 fold) and about 140% (2.4 fold) higher than that observed for the WT *Picochlorum* strain (1.65% dry weight) grown in UPA media at about 18° C.

The total fatty acid analysis of the three algal mutant strains (Strain 1, Strain 2 and Strain 3) showed production of EPA content of about 3.25%, about 4.17% and about 3.47% as dry weight of the cell respectively in growth (exponential phase) at about 12° C. to 24° C. (Table 8). The EPA content is about 188% (2.9 fold), about 269% (3.7 fold) and about 121% (3.1 fold) higher than that observed for the WT *Picochlorum* strain (1.13% dry weight) grown in UPA media at about 12° C. to 24° C.

The total fatty acid analysis of Strain 1, Strain 2 and Strain 3 mutants showed production of EPA content of about 3.9%, about 4.1% and about 3.1% as dry weight of the cell respectively in growth (exponential phase) at about 28° C. to 30° C. The EPA content is about 178% (2.8 fold), 193% (2.9 fold) and about 121% (2.2 fold) higher than that observed for the WT strain (1.4% dry weight) grown in UPA media at about 28° C. to 30° C. (Table 9).

Thus, EPA accumulation in exponential growth phase is further enhanced in all the mutants upon lowering the growth temperature to 18° C. and the mutant referred to as Strain 2 shows up to a maximum of about 5.83% dry weight EPA.

Example 8: Transcriptome Analysis of the Algal Mutant Strain

Transcriptome study growth conditions in ePBR, RNA sampling and RNA extraction:

For the Transcriptomics studies, WT and Strain 2 cells were inoculated at a cell density of about $2\times10^8$ cells per ml in e-PBR in triplicates for the experiment. The media used was UPA as mentioned in Table 1. The volume of the culture was 500 mL and depth was 20 cm. The growth conditions were 12 hour light and 12 hour dark sinusoidal cycle with the peak light intensity of 1200 μmole/s/$m^2$. The temperature was kept constant at 28° C. for growth till cell density increased to about $1.5\times10^8$ cells per ml. Throughout the experiment, the pH was maintained at 7.5±0.5 by $CO_2$ sparging. The culture was mixed at 400 rpm constantly. Once the cell density reached about $1.5\times10^8$ cells per ml, both the WT and mutant cultures were exposed to a temperature of 18° C. This low temperature shock was subjected for about 24 hrs. After 24 hours of temperature shock, samples were harvested for both the strains from each of the e-PBRs. The culture was centrifuged at 7000 rpm for 10 minutes and pellet was snap frozen in liquid nitrogen and stored in −80° C.

RNA was extracted from the frozen samples using liquid nitrogen crushing and TRIzol (Ambion) method. It was column purified using RNeasy mini kit (Qiagen). The Quality and quantity of extracted RNA was checked on Nanodrop and on 1% agarose gel and then sent for RNA sequencing.

TABLE 10

Comparison of mRNA transcripts of SDP1 gene (Triacylglycerol lipase) in wild type and the mutant Strain 2 at about 18° C.

| Sequence ID | Description | Gene function | WT transcript count | Mutant transcript count | Log fold change |
|---|---|---|---|---|---|
| SEQ ID No. 1 | Lipid metabolism | Triacylglycerol lipase SDP1 | 476 | 116 | −2.3 |

TABLE 11

Differential gene expression analysis of nitrogen accumulation gene clusters demonstrating positive fold change (Upregulation) in the mutant Strain 2 at about 18° C.

| Sequence ID | Description | Gene function | WT transcript count | Mutant transcript count | Fold change |
|---|---|---|---|---|---|
| SEQ ID No. 2 | N-metabolism | Nitrate reductase | 16 | 7660 | 8.55 |
| SEQ ID No. 3 | N-metabolism | Ammonium transporter | 209 | 24243 | 6.5 |
| SEQ ID No. 4 | N-metabolism | Nitrite reductase | 239 | 11472 | 5.24 |
| SEQ ID No. 5 | N-metabolism | Nitrate transporter | 69 | 3467 | 5.305 |
| SEQ ID No. 6 | N-metabolism | Urea carboxylase | 173 | 4061 | 4.2090 |

TABLE 12

Upregulation of gene clusters related to PUFA synthesis in the mutant Strain 2 at about 18° C.

| Sequence ID | Description | Gene function | WT transcript count | Mutant transcript count | Fold change |
|---|---|---|---|---|---|
| SEQ ID No. 7 | Fatty acid metabolism | Δ-9-desaturase 3 | 10 | 905 | 90 |
| SEQ ID No. 8 | Fatty acid metabolism | Δ-9-desaturase 4 | 12 | 2313 | 195 |
| SEQ ID No. 9 | Fatty acid metabolism | Δ-12-desaturase 3 | 15 | 469 | 31 |
| SEQ ID No. 10 | Fatty acid metabolism | Δ-12-desaturase 4 | 13 | 490 | 38 |
| SEQ ID No. 11 | Fatty acid metabolism | A-15-ω3-desaturase | 21 | 233 | 10 |

Transcriptomic analyses of Strain 2 and WT *Picochlorum* at 18° C. revealed altered expression of the following genes/pathways in the mutant Strain 2 when compared to WT *Picochlorum* strain, particularly as follows:

1) downregulation of mRNA transcripts of Triacylglycerol lipase gene (SDP1) by about 2.3 fold (Table 10);

2) upregulation of mRNA transcripts of Nitrogen metabolism genes by about 4.2-fold to about 8.55 fold (Table 11); and 3) upregulation of mRNA transcripts of PUFA synthesis genes by about 10 fold to about 195 fold (Table 12).

REFERENCES

For Lipid Estimation:

Ramanathan Ranjith Kumar, Polur Hanumantha Rao and Muthu Arumugam. 2015. Lipid extraction methods from microalgae: a comprehensive review. Frontiers in Energy Research 2(61):1-9.

For Gas Chromatography:

Laurens, L. M. L.; Quinn, M.; Van Wychen, S.; Templeton, D. W.; Wolfrum, E. J. "Accurate and reliable quantification of total microalgal fuel potential as fatty acid methyl esters by in situ transesterification." Anal. Bioanal. Chem., 2012; 167-178.

Van Wychen, S.; Laurens, L. M. L. Determination of Total Solids and Ash in Algal Biomass. NREL/TP-5100-60956. Golden, Colo.: National Renewable Energy Laboratory. 2013.

Christie, W. W. Lipid Analysis: Isolation, Separation, Identification and Structural Analysis of Lipids, 3rd ed.; Oily Press: Bridgwater, England, 2005.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A mutant algal strain comprising upregulated urea carboxylase encoded by SEQ ID NO:6, upregulated Δ-15-ω3-desaturase encoded by SEQ ID NO:11, and downregulated triacylglycerol lipase encoded by SEQ ID NO:1, wherein the mRNA transcripts of genes encoding these enzymes are compared to a wild type algal strain.

2. The mutant algal strain of claim 1, selected from the group consisting of: *Picochlorum* sp., *Nannochloropsis* sp., *Chlorella* sp., *Chlamydomonas* sp., and *Nannochloris* sp.

3. The mutant algal strain of claim 1, wherein mRNA transcripts of the gene encoding urea carboxylase are upregulated by at least about 2 fold, mRNA transcripts of the gene encoding Δ-15-ω3-desaturase gene are upregulated by at least about 5 fold, and mRNA transcripts of the gene encoding triacylglycerol lipase are downregulated by at least about 1.6 fold, as compared to the wild type algal strain.

4. The mutant algal strain of claim 1, wherein mRNA transcripts of the gene encoding urea carboxylase are upregulated by about 2 to about 9 fold, mRNA transcripts of the gene encoding Δ-15-ω3-desaturase are upregulated by about 5 to about 15 fold, and mRNA transcripts of the gene encoding triacylglycerol lipase are downregulated by about 1.6 fold to about 5 fold, as compared to the wild type algal strain; or wherein mRNA transcripts of the gene encoding urea carboxylase are upregulated by about 4.2 fold, mRNA transcripts of the gene encoding Δ-15-ω3-desaturase are upregulated by about 10 fold, and mRNA transcripts of the gene encoding triacylglycerol lipase are downregulated by about 2.3 fold, as compared to the wild type algal strain.

5. The mutant algal strain of claim 1, further comprising one or more proteins selected from the group consisting of: upregulated nitrate reductase encoded by SEQ ID NO:2, ammonium transporter encoded by SEQ ID NO:3, nitrite reductase encoded by SEQ ID NO:4, nitrate transporter encoded by SEQ ID NO:5, Δ-9-desaturase 3 encoded by SEQ ID NO:7, Δ-9-desaturase 4 encoded by SEQ ID NO:8, Δ-12-desaturase 3 encoded by SEQ ID NO:9, and Δ-12-desaturase 4 encoded by SEQ ID NO:10, wherein the mRNA transcripts of genes encoding these proteins are compared to the wild type algal strain;

wherein if upregulated, mRNA transcripts for the gene encoding nitrate reductase are upregulated from about 4 to about 12 fold, mRNA transcripts for the gene encoding ammonium transporter are upregulated from about 3 to about 9 fold, mRNA transcripts for the gene encoding nitrite reductase are upregulated from about 3 to about 9 fold, mRNA transcripts for the gene encoding nitrate transporter are upregulated from about 3 to about 9 fold, mRNA transcripts for the gene encoding Δ-9-desaturase 3 are upregulated from about 50 to about 120 fold, mRNA transcripts for the gene encoding Δ-9-desaturase 4 are upregulated from about 150 to about 250 fold, mRNA transcripts for the gene encoding Δ-12-desaturase 3 are upregulated from about 15 to about 45 fold, and mRNA transcripts for the gene encoding Δ-12-desaturase 4 are upregulated from about 25 to about 60 fold, as compared to the wild type algal strain.

6. The mutant algal strain of claim 1, wherein mRNA transcripts of genes encoding nitrate reductase, ammonium transporter, nitrite reductase, nitrate transporter, urea carboxylase, Δ-9-desaturase 3, Δ-9-desaturase 4, Δ-12-desaturase 3, Δ-12-desaturase 4 and Δ-15-ω3-desaturase, represented by cDNA having SEQ ID Nos. 2 to 11, respectively, are upregulated and mRNA transcripts of the gene encoding triacylglycerol lipase represented by cDNA having SEQ ID No. 1 is downregulated, as compared to the wild type algal strain.

7. The mutant algal strain of claim 1, wherein the mutant algal strain is acclimatized to temperatures ranging from about 10° C. to about 37° C.

8. The mutant algal strain of claim 7, wherein the strain is acclimatized to temperature ranging from about 10° C. to about 30° C.

9. The mutant algal strain of claim 7, wherein the strain is acclimatized to temperatures ranging from about 10° C. to about 24° C.

10. The mutant algal strain of claim 7, wherein the strain shows about a 2 to about 5 fold increase in Eicosapentaenoic acid (EPA) content during growth phase as compared to the wild type algal strain;

wherein the strain produces about 3% to about 6% EPA of dry weight of the cell during growth phase;

wherein the strain shows about 15% to about 25% increase in total lipid content as dry weight of the cell as compared to the wild type algal strain;

wherein volumetric productivity of the strain is increased by about 15% to about 60% as compared to the wild type algal strain; and wherein doubling time of the strain is reduced by about 10% to about 50% as compared to the wild type algal strain.

11. An algal cell population produced by a method that comprises:

(a) subjecting a wild type algal cell population to mutagenesis;

(b) following step (a), subjecting the algal cell population to growth cycles in alternating turbidostat and batch modes to obtain a modified algal cell population; and (c) subjecting the modified algal cell population in batch mode to alternating snap dilution and growth cycles;

wherein steps (b) and (c) are conducted in a controlled environment of temperature ranging from about 10° C. to about 37° C. and light intensity of about 200 μmoles/s/$m^2$ to about 1200 μmoles/s/$m^2$, to produce a mutant algal cell population comprising the mutant algal strain, wherein the produced algal cell population shows about 2 fold to about 5 fold increase in EPA content during growth phase as compared to a wild type algal cell population.

12. The algal cell population of claim 11, wherein the algal strain in the population has a doubling time reduced by about 10% to about 50% and volumetric productivity increased by about 15% to about 60% as compared to the wild type algal strain.

13. A method of producing polyunsaturated fatty acid (PUFA), said method comprising culturing the mutant algal strain of claim 1 to produce the PUFA.

14. The method of claim 13, further comprising isolating the PUFA from the culture, wherein the mutant algal strain is obtained by culturing the mutant algal strain of claim 1 to produce biomass;

wherein yield of the biomass is about 15% to about 60% higher as compared to a method employing a wild type algal strain;

wherein yield of the PUFA is about 2 fold to about 5 fold higher as compared to the method employing a wild type algal strain; and wherein the PUFA is EPA.

15. A method of producing biomass, said method comprising culturing the mutant algal strain of claim 1 to produce the biomass.

16. The method of claim 15, wherein yield of the biomass is about 15% to about 60% higher as compared to the method employing a wild type algal strain.

17. The mutant algal strain of claim 1, wherein the mutant algal strain is a *Picochlorum* sp. deposited with CCAP and having accession number CCAP 6079/2 (*Picochlorum* sp. CTM1), CCAP 6079/3 (*Picochlorum* sp. CTM19), or CCAP 6079/4 (*Picochlorum* sp. CTM20).

* * * * *

SEQUENCE LISTING

<160> NUMBER OF SEQ ID NOS: 11

<210> SEQ ID NO 1
<211> LENGTH: 2265
<212> TYPE: DNA
<213> ORGANISM: Picochlorum strain
<220> FEATURE:
<221> NAME/KEY: gene
<222> LOCATION: (1)..(2265)
<223> OTHER INFORMATION: SDP1 cDNA

<400> SEQUENCE: 1
atgtcggcga ggccagttgg aggtcaaatt ctgagaaaat ggttatttcc tattattgac 60
atacgacggt ttcatgtcgt agcagagttt ttgttgctaa acctggttgc atgcgtgaat 120
tctgcagctt ttcttgtggt atggtctgga atatcttctg cgagaagggc ttggaaatcc 180
aaaaaggacc caatagagca gcaacggaag agattacgag cagaaatggt ctccagcaag 240
agttatttcg aatggtctct cgcagctgca aagttggatg cattggaagg cacggatcaa 300
gaggcccgat ggagacagga aactgaattt tatgacagac gtcttcttga ggacaaggtt 360
gcgcatttgc gcaaaatcaa aaactcaggc ggcggtgtac tcgaccagat gttttctatc 420
agggccgatt tgctgcgaaa cctggggaat atcaccaact ctgagctaca cgagcatttc 480
ccagttgtgc ccagaccgat aagagattat atcgacgaag ttaaggggca gttgcaagat 540
attacttgga ctagagatat tccattggag gatcgcgtgg ccttcttgaa ggaaactcgc 600
catgcttttg gaagaactgc tcttgttatg tccggtggtg gtactttagg ttctttccat 660
ttgggagttg tcaaagcact cctacaacat agattgttgc caagggtact ggcaggtact 720
tctactggag ctattgtagc agcaattgcc gcgaccagaa atgatagcag tttaaatgag 780
ttttttgagt ctttgccaaa aatggatttg ggattcatgg ttcctcaaag ttccattcac 840
gttttgaaat atgatggcaa aaaaccccaa agaaaacaga tgaacatccg aatactgcgc 900
cagcttctcg gggatctgac atttttggag gcttatggag caactggacg agttttgaat 960
ttatcagtac atacattgga ttcacaagat cctccaagat tactaaatta tctgacctct 1020
cctgacatat tgatttggtc tgctgttgct gcagctgctg gtttgcctct cgcaaatggc 1080
aaggaaggtt tcatcttatt tgcaaaagat actgaaggcc gtatcattcg ctttgcaacc 1140
aagggaaaag agccacaaca ttattcagat caccagcatt catcagtttt gtgtaaattt 1200

```
ctgcctatga aatatacatc gaatgcagct tcgatgtcac tgcctggcag gtttctaaat   1260

atgttagaaa ccaacacatg gcagtcagta gatttagttt tgccagctga tgacttgcca   1320

tttaaaagct tgagcgagac cttttcagtc aatcacattc ttgtttccca aacagatcca   1380

catatcgtgc ctttaatgaa tattaagaag catcttggtg tctgcggcca agtggcagaa   1440

gcagagctaa ggcatagatg tctgcaagct cttgatgttc tcccaggaca aagccgtcct   1500

cgctggcttc gccgtatggc tcagccttgg gaaggtgatg tcacaatatc accaaaggag   1560

tttttgctgc agattcaagg tgttatatta gtctcgtcta atgagaatat gctcaaaatt   1620

gccagggaag gagagattgc aacgtgggca aaattgtctg caattcagtg taattgtgga   1680

atagaagtag cattggacga atgcatccaa actgcttact tgcagaaaag aggaggtaaa   1740

gatgatacag tatcgtcaca ttttggagac gccaatgcat caattagttt gaacaaacta   1800

aagcataata atggacctga tgagcataca ttcggacatg ctgcacaata tggcagcaag   1860

ggtggattga tgagtggtgg ttatggcccg ttaactggaa aatttagtag caatgtatgc   1920

agtgagagac agaggttgtt agactgtaac aattccattg agaagaaagg acgcgttgaa   1980

atggttgact gtattaatga caccccattt tctccgcgag aatcggtgtt gattctcccc   2040

tatgggacaa tgaaagacaa acaatacaaa gagaaaaacg tcagagatga tgcaatattt   2100

cgatatgaaa atcaattttc attgaaacaa aatgcaatga acgattgtat tgactattct   2160

gcgaatcctt ttggcaagaa tgatgctctt gagtctagca tcataaatga catgggaact   2220

aatactctgc tatcccgcag gtcccttgat gttattgccc cttga                   2265
```

<210> SEQ ID NO 2
<211> LENGTH: 2601
<212> TYPE: DNA
<213> ORGANISM: Picochlorum strain
<220> FEATURE:
<221> NAME/KEY: gene
<222> LOCATION: (1)..(2601)
<223> OTHER INFORMATION: Nitrate reductase cDNA

<400> SEQUENCE: 2

```
atgactgtgg caattgagga agtctctgca gaaagtatac agagagcaaa tggccaaaag     60

aagaatgcta tggtgtcagc gagagagaat acgatcccag ggcaagtgga gacttccgtt    120

cccaccatac ttaatgaaat cccaaaggaa aaggtacctt ctaacactgg ccaaattgca    180

aaggaagatt taaataccaa agacgaatgg atatcaagag acaaaaatat gataaggcta    240

acaggtagac atcctttcaa cagcgaacca ccacctgcat ttctgaaaaa gagttttata    300

actccagttc ctttgcatta cgtgaggaat catggtgctg tcccccatat ctcttgggat    360

gaccacaggc tcactgtcaa tggactcgtt ggagaatctc gaacatttac catggacgaa    420

attgtgaaaa tgcctgccat ggatgttacc tgcactctta cctgtgcagg caaccgtcgt    480

aaagagcaaa acaagataaa aaagacaatt ggatttaatt ggggcgcttc tggaactggt    540

tgctctattt ggactggtgt ccgtttgggt tatttgcttt cgttgtgcaa agtgaatact    600

gcagggacag cattacacgt ttgcatgcga ggtcccaagg gtgagcttcc gcggggagat    660

gatgggtcgt atggcacttc aatatctctt gagcgtgcca tgaaccctgc ctatgatgtg    720

atacttgcct acaaacagaa tggtgagctg ctaagccctg atcatggatt tcctttgcga    780

gtgattattc ctggctacat aggaggtcgt atgataaagt ggattgaaga aatcactgta    840

tcggaaactg aaagcaacaa ttattatcac tttcacgaca atcgaattct cccctcgcat    900
```

```
gtcgatgaag agacagcaaa cagagatggt tggtggtatc accctgactt tatattcaat    960

gatcttaaca tcaacagtgc agtgatgtac ccaggacatg atgaagttat tccactcaga   1020

tgcaacacaa aggtggaaat agggggctat gcttattcaa acggaaacaa aattattcga   1080

tgtgaaataa gcttggataa tggtaacact tggaaactta ccgaaattgt tcacagggca   1140

aagccaaatt cttatggaaa aatctgggca tgggtatggt ggaagattca agtaaatgtg   1200

gtggacctat tcaaatccac tcaagccgtt tgccgggctt gggacagtac tatgaacaca   1260

cagccaaatt cctttacttg gaacgtcatg ggtatgggca acaactgcac ctatattgtc   1320

agaattcacc cctgtgccac atcagatggg tatttgggaa tcaaattcga acaccctact   1380

gttgctggac atgctaatgg aggttggatg gatgcaaatg acggtattag ggcaggagag   1440

caaagtccaa atgacgaact tggtaaaaac aacaataata agaataaaat ggtcgaggat   1500

aataataagc tcaagaaata caccatgaaa gaagtcgaga agcataatag tagagaaagt   1560

gcttggtttg tctacaatgg cttagtgtat gatgcaacac catttttgga aaagcatcct   1620

ggtggtgcag atagtattct gcttgcagct ggtaccgatg caactgaaga tttcgatgcc   1680

atacactctg gaaaggcgaa acaaatgtta gaggaatatt gcataggaca gctcgtagaa   1740

tctttgccgg aatcacaaca aaatatgacc tatccattgc tcaacaatcc tatcgaagaa   1800

gaagctgaaa tgattgccct taacccaaag aaacgtttgc cttttcgttt gattaagaaa   1860

gatagtctca gtcacaatgt atgtcgtttt cgctttgaat tacaatcgcc ccgacacaaa   1920

tttggattac cagttgggca gcacatcttt ttgtatgcca aatcaatgga taagcttgtg   1980

atgagggctt acacgcctac gtcgtctgat gatgatttag gttacttcga attggtcatt   2040

aagatttatc gagcaaatga aaatcctcgg tttcctgaag gtggcttgat gtctcaatac   2100

ttagattcaa tggaattggg ccagacgatt gatgtgaaag gtccagtagg tcacatgatc   2160

taccgaagtt taggacactt cacacttgaa ggaagacctt gctcagcaaa gaaatttaac   2220

atgtttgctg gaggcacagg cattacccct ttgtaccagg ttattaagag cgtcctcaag   2280

aatgctaatg acagaacaga tatgcgtctg ctgtacgcca atcagactcc agatgatatc   2340

cttttgaaag aagaacttga tgaacttgct gctaatcatt caaatttcag tgttagctat   2400

acagtggatc gtatccctga ggaactagaa tggaatcatt ttagaggaca catgaattac   2460

gagatgatca agagctgtat gtttcctgcc gatgattcca cgatgtgctt gatgtgtggc   2520

ccaccaccaa tgctgaagtt tgccatcatc ccatctttgg ataaactagg tttcaagaat   2580

aaccaaatga ttgaattttg a                                             2601
```

```
<210> SEQ ID NO 3
<211> LENGTH: 1512
<212> TYPE: DNA
<213> ORGANISM: Picochlorum strain
<220> FEATURE:
<221> NAME/KEY: gene
<222> LOCATION: (1)..(1512)
<223> OTHER INFORMATION: Ammonium transporter cDNA

<400> SEQUENCE: 3

atgagtgata cgatagcctt cgagaacctc gagcaggttt ccgagctggt caatgacggc     60

accttacacc ttgccgctga tgctgatgca caatggctgt tgcaaagcgg ttatatggtg    120

ttcttcatgc aagctggttt tgctatgctt tgcgctggtt ctgttcgagc taaaaatgcc    180

aagaacatca ttcttttgaa cattcttgat gcctgctgtg gaagtctttg ctggtgggct    240

actggttggg cctttgccta tggtgataat ctgaattgca atgaaggtgt ttgtacctta    300
```

```
cagaatggaa atgctgctcg attcagtggc agcaagtatt tcttcctcaa taatcttcct    360
tctggtgatt atgctagttg gttctatcaa tttacctttg cagcaactgc agctacaatt    420
gtatcaggag ctgttgccga acgtaccaaa ttccaggctt atcttatgta tgaaggtttg    480
cttgtcctta tcgtgtatcc tattgttgct cactgggttt ggtccagcac aggatgggca    540
actgcattcc ctgctacaat aaatgaagaa accggagaaa ctctgtcttt cttgtttggt    600
accggtgtat atgattttgc tggtgacggc cctgtccata tggtgggtgg ctttgcgtct    660
atgggtgcgg cttatattct gggacctcgt attggtcgtt ttgatgctga tggtaaccct    720
gtagacatgc cgggccacaa cgcctcatta acacttcttg gtgttttctt cctctggttt    780
ggatggtatg gatttaatac tggatctact cttgccatct ctggaggtac ttcagatctt    840
gcagctacag ttgctattaa caccactctt ggtgcagcta ctggtgcttt gtcaactctt    900
ttcatctcct acttagtcag ttatctacag agtggaactt atctctatga cttgcttcag    960
gtcggaaatg gtgctcttgg tggacttgtt gctgtgactg gcggtgctgg ctacattcgc   1020
ccctgggctg ctttcatcgt aggaattatt ggtggttttg tttactttgg atcctctaag   1080
ctcatcttga atgttatgaa aattgatgac cctgtggatg ccattgctgt gcacgctttc   1140
tgtggcatgt ggggtttgat tggaacagcc gcattcactg ctcctgaatt tgcagctgac   1200
tctggagcct atggtttcat tatgggcgga aaaagttctg gtggcaagct cctagcagct   1260
gctctggtgt acattcttgc tattgcagcg tggactcttg gaattactct tccattcttc   1320
tatgccatta agaaacttgg gcaattccgt gttgaccctg aagttgaggc agctggtctt   1380
gatgtgtctc accatggtgg ctctgcttat ccccacgatc ctacatctgc aaaggccagt   1440
atgactatca attctgaaat gatcgatcgt aagattgaag aggctttggc gaaagccaag   1500
ctcaatgctt ga                                                        1512
```

```
<210> SEQ ID NO 4
<211> LENGTH: 1779
<212> TYPE: DNA
<213> ORGANISM: Picochlorum strain
<220> FEATURE:
<221> NAME/KEY: gene
<222> LOCATION: (1)..(1779)
<223> OTHER INFORMATION: Nitrite reductase cDNA

<400> SEQUENCE: 4

atgtggatgc gtcggaatgg gactcccttt actccaggat ctttctctag atcaaacctg     60
agatgtaacg tgacactacg ggcgacttcg actccaattc agtcacataa tcctgaacat    120
gggtctttag acgacatcat tgagtctatg ggaattgata tggcagtatc tggccttcgt    180
tatctttcgg aagatgctca gttttctgtc gttcagctga gagccttgtc caaaaaggca    240
aacaaattcg agaaagtgaa ggcaaagaaa tgtggctcga ccatgtggag agaggttgga    300
gaattatcca gcctgatcag agagggtaaa acaagttggg aagacttgga gctggatgat    360
attgacattc gtctcaagtg ggctggtctt ttccatagga gaaaacgtac tcctggtagg    420
ttcatgatga gactgaaaat tccaaatggt gagcttactt ctgaacaact tcgtttcatg    480
ggaacttgca ttgcaaagta tggtgaacaa ggttgtgggg atataactac tcgtgccaac    540
atccaattgc gaggaattgg attggaagat gcggaagaga taatcgaggg actgcaaaac    600
ctgggtctga gcaatgtaat gagtggaatg gataatgtga gaaacatcac gggcagtcct    660
atcgctggga tagaccccca tgaaatagta gattcaagac cactttgtca tcaactcaat    720
```

```
gctgccatta ctgcccatgg aaaggggaac ccagagctgg ccaacttgcc caggaaaatt     780

aatattggta tctcaacaag ccgagatgac tttgctcatt gtcatataaa tgacgttgga     840

ttaaaggtag ccatttccaa aaacgatgag ataggtttta atgtagaact aggaggatat     900

tttagtatca agagaaatgt aatgagcata gatggagata cctttgtgcg atatgatcaa     960

gtagtgccat attgccttgc tctgcttgaa gtgttccgag actatggggc tcgccaggac    1020

aggcaaaagg ctaggttgat gtggttagta gaagagtggg gcatcgaaaa gtttcgcaat    1080

atgatcgagg cacgaatggg gcagaaatta agcaatgctg ttcccgttga atattctgag    1140

gattggcaga ggcgtgatgt cttgggtatt catccacaga agcaagaaaa gctgttctgg    1200

gtcggtgctt gtgttcctgt tggtcgactc caaactactg actttttcga actcgctgaa    1260

gttgcagaca actatggaga tgggacggtg aggctaagtg tggaggagaa tgtaataatc    1320

ccgaacgtgc atgaaagaca tttggatgag atacgtgagc atccattgtt ccaaagattc    1380

cctatagaag gagggcctct tttaaggggc cttgtatctt gtacaggagc tcaattttgc    1440

tcacttgcac tcatagaaac taaaaaccgc gccttaaaga taattcaaac acttgaaaat    1500

gagctaacaa taccaaatac ggttcgaatc cattggacag ggtgccccaa ctcatgtgga    1560

caagctcaag taggggacat cggtctcatg ggtgcacctg caaagttgga tggaaaagcg    1620

gtggagggag tccgcatcat gataggaggg aaaattggtg aagacccgag actggcctct    1680

gatttcgaga attctgtccc atgtgatgaa atccatttgt tgcctaaact tcgaaaaata    1740

ttgatcgacg aattcggtgc ggaattgaaa gaaacctag                           1779
```

<210> SEQ ID NO 5
<211> LENGTH: 1677
<212> TYPE: DNA
<213> ORGANISM: Picochlorum strain
<220> FEATURE:
<221> NAME/KEY: gene
<222> LOCATION: (1)..(1677)
<223> OTHER INFORMATION: Nitrate transporter cDNA

<400> SEQUENCE: 5

```
atggggaaag aagaaggcag cgatgacttc tccagagaag agaatgtctt tgatttcaag      60

gttccagttg actcagaaaa ccgagaggag ggtggggata tgtttgacaa aagaaaagga     120

acaaaggacc agatcgaagg tgaaagagga gctgcaaact ccatgacatc tctaattgag     180

acgagaagtt tcacaagcac tcgaattgca ttgaatgcat gtctctctcc ctcgaagaaa     240

tgtgaagata aattttacca actttccaca catttatttt ccgttgtgac tgattcgcag     300

atccaaagtc ttgaaacctt ttttgcaacc tttactgcac cgccattgat ccctgttatc     360

cgaaatgacc ttaatctcac aaaagaagat cttggaggag cagccattgc atctgtgacc     420

ggtgctatct tctcccggat tttgattggt gttgtatgcg acagttatgg accacggtac     480

ggccatggct tcttacaact tttgacttgc accgctacat acggaatggc tctcgtcaat     540

aatagtgctg gttttattgt atgccgtatg atcattggtt tcagtttggc tacatttgtc     600

tgttgccagt actggtgttc ggtcatgttc aatgtccgca ttgttggtac agcaaatgcc     660

acaggcggag gctgggggaa cttaggtggt ggtgttactc aattgataat gccattcata     720

tatcaaggta tagaaaatac acaaccatcg ttcattgctt ggcgatgtgc atttttgatt     780

ccagcttcag ctcaatacat aatgggaatg atggtcttaa ttttcggtca agacttacct     840

gaaggaaatt atgcagaatt gcgccaaagt ggtcaaaagc ccaaagcaaa ttcaaaacga     900

gaattccttg cggctgtgaa aaattatcgt acatggattt tggtgctgaa ttacggctat     960
```

```
tgctttggtg tagaactgac agtgaataac aatatctctc cttatttgta tgatcagttc   1020

gatatctctc ttggtcttgc tggaactctt ggatcctgct ttggtttgat gaacatcttt   1080

gcaaggtccc ttggtggcat aacctctgat cttacagtaa aacgctatgg catgcgcgga   1140

cgactttgga cctactggtt cacgcagacc atgggcggtg tcttctgtct gattatgtat   1200

tttacccgca atagccttgg cgcaacgatg cctgtggtag tatttttctc cttatttgtg   1260

caaatggcag aaggcgcatg ctttggcatt gttcctttca ttacccgaag aggacttggg   1320

gctgcttcgg gtttcgttgg agctggtggc aatactgggt cagcagttac ccaggcaatt   1380

ttcttcactg acagcagtct gacaacagca gaaggctgga aatggatggg tgttatggtg   1440

atagcagtga gtctgacgtt aactctgatt catttcccca tgtggggatc catgctcctc   1500

cctggcaacc ccaaacacac tgaggaagag tattatgcta aagactatac caccgaagag   1560

aaggagcaag gtcttcatat ggttgattcc aaatttgcga atgaatcaag gtctcaaaga   1620

ggtttcaagg cagcgcttca agaggatgat agcggtaaca ttccctcgtc ggtgtaa      1677
```

<210> SEQ ID NO 6
<211> LENGTH: 5793
<212> TYPE: DNA
<213> ORGANISM: Picochlorum strain
<220> FEATURE:
<221> NAME/KEY: gene
<222> LOCATION: (1)..(5793)
<223> OTHER INFORMATION: Urea carboxylase cDNA

<400> SEQUENCE: 6

```
atttcaatcg tatttgttgt gcattttggg ccccaaccga acatcgatcc aaacttcgcg     60

attgcaacat ctgacatcag tccttggcag ttgcaccttg gtttcatgat ggagcatcac    120

aaatcaaaaa ggattactaa aattctcatc gctaatcgtg gagagatcag ctgtagggct    180

cagagagcat gtgcaaagct tggcatccct tgtgtcgcag tttatacatc atcagacgcc    240

ttgtcccttc atgttatacg ggctgaagaa tctgcatatc ttggtaaatc tccaaaagaa    300

tatttgaatg caaaaaggtt gattgaaatt gcaaaagaaa cagcctgtga tgctgttttc    360

ccaggttatg gattcttatc tgagaatgct gaatttgcag aggattgtga tgcagccggc    420

atagagttta tcggtccaac tggttctaca atgcgagcct ttgctcagaa acatactgcc    480

aggaaacttg ctcaagatgc tggtgttcct gtacttcctg gaacagaatt gctttcaagc    540

agtgatgaag ctcttaaagc ttcaagagat atcggtcttc caattttgtt gaaagctaca    600

ggtggtggtg gtgggattgg aatccacatt tgtcgcacag aggatgatgt cgttgaaaaa    660

tttaattcag ctgctcggca aggagaggca gcttttggaa attctggagt ttttattgag    720

aaatatgtag aaaaagctcg acatattgaa attcaaatat ttggagatgg ctgcggaaat    780

gtggcaactt ttccagagcg ggaatgctcc atccagagaa gacaccaaaa agttttggag    840

gaaacaccgt ctccctttgt ctccctgcat ccagagatca gacaatcttt gcagaaaaca    900

gcacgagcac tagcatcttc gattaaatat cgttcagcag gcacagttga atatatatta    960

gacgatgaaa ccggagcatt ctactttctg gaggtcaata ctcgcctgca agttgaacat   1020

gggataactg agcttgtttc tggtgtagat atcgtcgctt ggcagtttca attacaagga   1080

gcattgcctc caaaacaatg tgaaatcggg tcagtactgc ccaaagatat atcaaatcta   1140

tctcttgatt tgcatggaag tgcaatcgaa gtccgtatat gtgctgaaga tccagctcat   1200

gggtaccgcc cttgcgctgg ggtacttggg gaggtctgct ggccaaatga tgaagtccgt   1260
```

```
gttgacacgt ggatcgagag tggctctgaa gttacatcat tttatgattc tttactcggg   1320
aaattgatgg ttcattcatc agaaggccga aatagtgcaa ttaaaaagat gcaaaaagca   1380
ttgaaatcca caaggttggc tggagtaact tctaatttag atctgttgcg agcaattgta   1440
tcaagcccaa aatttgtcga agggtcgacg accaccaagt tcctggatgg attagaacaa   1500
aacatcgagg caatagaaat aatcgagcct ggatttatga caagtgttca agattatcct   1560
ggtcggacaa agatgtggtc agttggtgtg cctccatctg gtccaatgga tagtctttcc   1620
catcgcatgg ccaatgcttt ggttggaaat tgttctgatg aagcagcctt agaaattgga   1680
ttggtaggtc caactatcag gtttttatca ccaagagttg ttgctgtttg tggatcaagc   1740
acaaccataa aattagatgg acaagaaatg cctcattcgc aatctttctc tgtctcggtt   1800
ggccaatcgc tatccattgg aaatcttgaa aatgcagctc gcgcatattt ggcgatatcg   1860
ggaggccttg acgttcctaa gtttcttggt tcacgctcga catttcctgc gggctgctta   1920
ggtgggcatc aaggtcgtgt gttaagagct ggtgacatgc tcccattagg ttctgttgaa   1980
aatcaggtac tggtcggtac caaggttcct gagatttggc gcccacccat gtcggatggt   2040
gagctatgga aaattaaggt acttccagga cctcaagcag atccagatta cttcacaaga   2100
gatgatataa gccaatttta ttctacagat tatgttgtcc atcacaactc aaaccgctta   2160
ggaattcgtc ttgaaggacc aaggcctaaa tttgcaagaa cagatggtgg tgaaggaggt   2220
tcacacccat caaatgtaca tgatcatgtc tacgcgattg gtacagttaa ttttactggt   2280
gacatgcctg ttgttttgat ggtagatggc ccatctcttg gtggatttgt ttgtccagcg   2340
actataatca ctagcgagct ttggaaaatg ggacaggtta aggcaggaga caaagtacgc   2400
tttatccaaa caactatcga ggaagcattt gctgaaaatc ttaagacaga tatgaaaata   2460
caattaattg aaaagatggc acatggcaag atcaatacaa aggatgcaga cgaacagctc   2520
aatagctttt gcccacaaat aaacaaaggt ccggaaacaa aagccgtgtt ggctaatatc   2580
gaaaaaactg aatctcatcc tggagctcag ataaggcttg ctggagaccg ctacatattt   2640
gtggaatatg gtccgatgga gctcgatcta aatttacgag tcagagtcga gcaactccaa   2700
gattggctct cctcaaaaca aatctccggt ttgattgaaa caagccctgg ggtaagaagc   2760
ttaatgattg aatatgatgc aaaaatactt gacttggaca agcttctaaa cattatattc   2820
tgtgccgaaa aagagcttga gcctgcgaat agattggtga ttccttcaag aataatatat   2880
ttgccacttg catttaatga ccgctggacc aaggatgcaa ttttgcgtta ctcaaaatct   2940
gttcgatctg aggctccata tttgccttca aatattcaat ttgtcgctga aaacaatggt   3000
attaaaggag gtgatgccat cagtaccatt caaaatatca ttgaatccgc ctcgtatatg   3060
gtaatgggcc tgggagacgt ttacttagga gctccatgtg ctgtacctat tgaccctcga   3120
catagactta ttgtgccgaa gtataatcct gcaaggacat acacaccaga aggggcggtt   3180
ggtatcggag ggtgctacat gtgcatttat ccaatgaatt ctcctggtgg atatcaactt   3240
gttgggagaa ctattccaat atggaattcg tataccaggg tcggtccatt cgagaaagga   3300
aagccatggc tgttacgaaa tttcgatcag atcaggtatt ttgtcgtatc ggaagacgaa   3360
ctagaagata tgaggcatga atttaaaaat ggaaagctca gactaaggat agaagagagt   3420
gaatttgata tggcaattta caatgatttt acacagagtg ttgaacaaga agtccaagtc   3480
tttaagtccc aacagaaaat ggcaatggaa aaaatgcttc gcctcgatgc tgagtcattg   3540
tctcgcttgg attcggctaa gaccttggat tcaacgtcta atgatagtat tagtattgaa   3600
gagatagaag atccatatca tgggcatggc ggaaatcctg tccgagctgc tgtaacaggg   3660
```

```
acagtttggg aagtccgagc taaggtgggg gatattgttg ctcctggaga tattctttta   3720

gttttagagg ccatgaaaat ggaattcgag gttgtatcct cttttgctgg acaaattaaa   3780

gatattgctg ttacaactgg tgatatgtta aacttcacct gtacaaagga gctgtctttg   3840

cttccttcac aaagactgca gaaaggtcga catgagcaaa atcataaagc tctacgaatt   3900

caatgcccat tcttctacac tcactgttta aattatattt tgaataaaac aatttacata   3960

gaaggagcta tcagctcaaa tagaagtgat gtgacacaac tgaagtcgac tgagtcaatg   4020

caaattttcc tttattttga aaataaacat tatatttatc ctaaagttag aattgttgtt   4080

ccaaagggac caaagatgct cacgactgag gaccttactc tcactgctct acgaaaagca   4140

tatgttgaag gcaggcaaac ccctacgacc gtctgtcagc atctcttgga taaaatagct   4200

tcatcacagg gcattttcat atcctctccg agagtttctg atgtactaga gcgatgcaaa   4260

attctggagt cccttccaga gaacaagcga ggcagacttt ggggcatccc attcgctgtc   4320

aaggataaca ttgatgtgga aggggagcca actacttgcg catgtcctga cttttccagg   4380

atagcaaaag ctagtgcccc aacagttcag gccattattg atgctggtgg tgtattttta   4440

ggcaaaacta atatggatca gtttgcatgt ggtcttgttg gaacacgtac tccatatggg   4500

atacctaaga acacttttga tgaccgcttt actccaggtg gttcttcttc tggatctgca   4560

gttgcagttg cggaaggtat ggtgacattt gcacttggaa cagatactgc aggatctggt   4620

cgagtacctg ctgggcagaa tggcattgta ggtatcaagc catctctagg acgtttttct   4680

acattgggtg ttgtcccagc atgttatcta cttgactgcg tatcgatttt tgcgttgaaa   4740

gtttcggatg ggactgaaat agctaggcta ttagaaaatc aaaatgtttc tgatcctaca   4800

tggagacctc agaacactga attgagaaac aaaagttttg tacccaaaca gaagtttaag   4860

ttcagtttgc ctgagcaaaa gttttggaaa tttgatggcc caggaggaga atctgtgcgt   4920

ttggcaatgg aagaagaaat gaaaagagca attgaaaggc tagttaattt aggaggggaa   4980

caagtccaaa tcgatttcac accttttgct gaaactgctg ttcttctata tggaggtcca   5040

tttgttgcag agcgctactc tggaattcgt tccttcttgg aagctcgagc cccagatttg   5100

gagcctccag aactggctga tatttctata gatcaaagaa tgcttaaagt aacacgatca   5160

atcatatcga aaactgaaca ttggggagct gcagatgttt ttgaggcttt tcaacaactc   5220

tcacaattaa aggcagaggc aagaactgag ctcagcaaga ttgacatttt agtagtacca   5280

acggtagctt ataattatac agtgagagaa atagtagaag aggaagatga acaagattat   5340

agagatatgc tttctggtaa agcaatgctg accaaaaatg caaacctggg acgattcact   5400

aattttgtaa acctgttaga tatgtgtgga atttctgttc caagtggaat cttggaaatg   5460

gaagcaaact gccctgaaaa gcatacacac aaaaaggctc gcaaaattaa aaataatgat   5520

aagaactcca atggcacttt ggtatctaac gaaagcggca agcaatctca aacaatctct   5580

ccgagagacc acttcttaga ggctacaggg aagcggtcag tgatgttgcc ttttggtgtt   5640

actctactag ggcctgcatg gacggatgac tttgttgctg gagtagcttc tctatatgaa   5700

gaggccacag ggttgggacc aggacctatt ggacatagag taactccata tcaaacaaca   5760

ggtaaagttc gaccccgaaa gcctgggatg tag                                5793
```

<210> SEQ ID NO 7
<211> LENGTH: 1465
<212> TYPE: DNA
<213> ORGANISM: Picochlorum strain
<220> FEATURE:

<221> NAME/KEY: gene
<222> LOCATION: (1)..(1465)
<223> OTHER INFORMATION: delta-9-desaturase 3 cDNA

<400> SEQUENCE: 7

```
attataagag actattaaca ggtatatgga gcattaattg attcgaaagc atactgaaag     60
tcgagtctat ctgaacgtta tctacggatt ctgaggatag tttgacgcca cagacgcgtg    120
tttttgattc tgttggcgca tttatttatc caaacaaacg aacaattctc tgaaagcttg    180
aaaaggaatt atggcgttgg ttcagacacg tactgtggct ctggggagtc tggttgctag    240
accggttgcg gtggagaagg gtcacgtgac cagcattcgt cagcgtatgg gggcgttgag    300
gaggacgaga gtgcgcgtag cgtctcctca gcggttggaa gagactcctt ttatgcaaga    360
ggatggtgtt cagccacctc agatgtcaga gctgtcttac aataagcagt atgagcagtt    420
gtttaattca ccagaggggt tgaatctgag aaaggctgtg gcaaagcctg tgatggaagc    480
tcaggcggat gaggaagggg cgaagaaggt gttcatgtct gatgtgtatg gattaccgaa    540
gaagaatctt ttcttcaaca gagagtataa tacgaatgat ttgatttatg ttgggttcat    600
gcttggcatg cacgggttgg cgtgcctggc gccaatgacc ttctcttggc caatggtgtg    660
gctcttcttg ggtcctattt tcgtgtctgg atgccttggt attaccctct cgttccatag    720
gcagctgtct cacagatcat tccagacacc aaagtggttg gagtacgttc ttgcatactg    780
tggtgtgttg gcagtgcagg gagatcctgc cgagtgggtg tccagccata gatatcatca    840
tcttcattgc gatacgccat tggatccaca ttctccatat gaagggttct ggtggtctca    900
tatgggatgg ttgttggatc acgagacaac gctggagaga gtgcatgaca gaaccaatgc    960
atcggatatg tacaaagacc cattctacag acatttggaa aagtattatg cgtggcacgt   1020
ggctgctcag tttgcagtgc tgtatgcgct tggagggctc cctgctgttg tgtggggagg   1080
tgcactccgc attgtgtggg tgtaccatat tacatggttt gtgaactctg cagcacatgt   1140
ctggggtaat cagacatata ataccggtga tttgtcgcga aataactggt gggttggtat   1200
tcttgcgttt ggagagggat ggcataacaa ccatcatgcg tttgagtttt ctgctcggca   1260
tgggcttgaa tggtggcagt ttgatatgac gtggatggtg attaaagccc ttgaagcgtg   1320
tggtcttgca acgaacatca agctgccctc tgagaagcaa aaggctcgat tggcactgta   1380
gatgatgcac atcgtccagg aattttcaac aacttatgct ttcttatttt ttttaaaccc   1440
tgtaaattca tgctgtcatc aaaaa                                         1465
```

<210> SEQ ID NO 8
<211> LENGTH: 2358
<212> TYPE: DNA
<213> ORGANISM: Picochlorum strain
<220> FEATURE:
<221> NAME/KEY: gene
<222> LOCATION: (1)..(2358)
<223> OTHER INFORMATION: delta-9-desaturase 4 cDNA

<400> SEQUENCE: 8

```
atatacgtta aatatatacc attgcaatct attattgcat ataatttggt ttgctgcgtg     60
aattcgtatc gaattgtggc gtattaagaa atagtgtagg atagaatact ttgtcgccat    120
ggcgaaatct gatactaaag ccgcaacaag tgctggaaat ggaactaaat ccactattgc    180
atctttgaaa gaagaaggta gccgtgcctt tgccatgaaa gagtatgatc gggctgtggc    240
agcatgggac aaggctctgg ctttggaaga tatttcgaaa tcagatgtag ctttgatcca    300
taataataag gcggcatgtc atatggtgag caagaattac aaggatgctg tatctgaatg    360
```

```
cagcgttgct cttgagacac aaccagaata ttttaaggcc tttattcgtc gctccaaagc    420
ctatgaagcc atgggaatgt acaaggaagc cctggccgat cttcagaaag caaacggact    480
ggatgctgca accgatgatt caagagctgc agagaaacgg gttcgtgatt tggcagcggg    540
taaaaaacct gcaggcatgg gaaatggctt ggcaagacgc tcaggagcaa gtgctgcaag    600
agcagccacc tctgggacca gtggtagagg gaactctctt gtaatgcgcg gagtacctgt    660
caaactaaca tttggtgatg atattcgtca atttaatctt gttcctggtg tgaagtattc    720
agagttattg gagtatgttc gctccttgtt tcccaaggct ggtcattttg tgctcaaata    780
tttggataaa caaggagatt tggtgactat tgcttccaag caagatctgc atgttgctat    840
gtctgaagcc atagatgcag ctggcaaagg cgcggctcga ggagctggtt ccattcctcc    900
tgttagatta catgcgattt cagtcgaatc tgcagaagat gtccccaaaa ttccagagga    960
tgagctacag cagcagcagc aatacatgaa agagctcttt gaacatctgc aacgtcagca   1020
ggcagctaag gacgcccaag caaatgcagc aaccgagcag caaccacccc aagttcaggt   1080
agatgaatgg ttgctcagtt ttgtggaaat gctaaaagaa tactgccact tggatgttga   1140
tcgtccatta gaagcacagg aaattggaca agatcgtttg aatgcagctt tccactcaat   1200
gatgcaaaat gaccccaaat cagaggaatt attggaccaa gcccatgata agttcaagga   1260
gcaagcttct ttggcaatgc tatgccaagc acaggttcat gaagcgaaag caacacgcct   1320
tatgtttaag gcagctgcag atagcacacc ggccacccaa attgctgcag atgtagagaa   1380
gcaccttgca gcagcagagg caaaggcaaa agaggccctt gcctattgtc ctgatatccc   1440
tgatggtttc ttaactctga ataacattca catggctaga gctaaactag ctgccgatta   1500
tctgattgaa gctgtacctc ccaaggaaga tattaaagat cctgtggaga aacaagaagc   1560
ggaagaggca gcagcacgag cagctgccaa aaaagcagca gatcgtgtca ctgctaagtc   1620
tgctgcggcg gcggatgctc acatggagcg tgcttatgct gagttagata atggaatgaa   1680
ggcattacct gcagaagagc gtgaccggga attaaagcct ctcaagccta tggccgagca   1740
agtccccgga gatcctgaga gtgaaactcc attgaaggca tccatgctga tcaatgcagg   1800
taacgcacgt tatgaacata gtattctgcg agctgcaggt ggattggaat ggcgcccccct  1860
gattgaagaa gcggctaagc ttttccgtga agctggagct gcagaaattg acattcgcaa   1920
tgcactcaaa ggacatccca tgtctgaaga gatggcagat ctcatcggac ctgagccaga   1980
tacagcccaa gaagacaata agaagacaga agaacctaaa ggtgttgctg cattgccaaa   2040
gaaaaagtag cgcacttcag ttcaatcttg atcattttca agatatctga actagttgtc   2100
ataaattgga aaacttattc tgccagagat ggatgattcg gggccaatca aagtagtcac   2160
aaaattgtac ttgcacgtct gtcaagtaat ccaagtagca atgaatacca cagcttaatg   2220
ccacagtttt ggttttcact tttatgttag gcataatgaa atgatcacga ttttctatat   2280
tatataattg ctgttataaa ttccatgaaa gtcaattgaa tatttgatta catgtaattg   2340
aaattttcaa tcaaaaaa                                                 2358
```

```
<210> SEQ ID NO 9
<211> LENGTH: 1282
<212> TYPE: DNA
<213> ORGANISM: Picochlorum strain
<220> FEATURE:
<221> NAME/KEY: gene
<222> LOCATION: (1)..(1282)
<223> OTHER INFORMATION: delta-12-desaturase 3 cDNA
```

<400> SEQUENCE: 9

```
atttcagcca agaagaatgt tctcaaagtg catgctgctg caccaattca ggttgagcag      60
atgtcaaacg ttggttacat gagtgatgag gagcgtgcag cccttgcaaa gcagttgggt     120
tacagaagca ttgggaaaga gcttccagac gatgtcacct tgtcagatgt gatcaagtct     180
cttccagaag aagttttcga aatcaaccca ttgagggctt ggtccgctgt tgcgctgact     240
ttggcatcta tggctgctgc tttgtatgcc atctccatct ccccatggta cctgctgcca     300
tttgcttggg cctttgctgg aactgccttc actggcttct tcgtggtagg acacgactgc     360
ggacatagat cgttctccaa aaacaagctt gtggaggaca tcgtgggaac actcatgttc     420
atgccattga tctatccatt cgagccatgg agaatcaagc acaaccagca tcatgctcat     480
acaaacaagc tggtagaaga cacagcttgg catccagtga aacgtgaaga catgaaagac     540
tggagcccag catacgcttg ggtatacaag accttttttgg gaactcctct gaaattgtgg     600
gcatccatcg gtcactgggc tgtgtggcac tttgacctga acaagtactc tgagaatcaa     660
aagcctcgtg tcatcatcag ccttgtagct gtggctgcct tcattgctat tggatggcca     720
cttattatta aatgtaccgg cttcactgga ttcctcaagt actggttgat gccttggctc     780
ggatatcact tctggatgag taccttaca gttatccatc acacagctcc acacattcca      840
ttcaagccag ccgagacttg gaatgctgcc aaggcccagc tttcaggaac tgtccactgc     900
gatttcccaa gatgggtaga gattctctgc cacgacatca gtgtgcacgt gccacatcat     960
gtcaatgcca agatcccatg gtacaatctc cgtgctgcaa atgaatccct tcgcaagaac    1020
tggggagagt acatgactga atgcgacttc aactggagaa tgatgaaaaa catcttcacc    1080
gagtgccacg tatatgatga gaaggataac tacgttccat tcgatttcga gaaggaggag    1140
ccaatgtttg cagttcagcg caaggtcttg cccaactcca tgtgaagatt tttcagcttt    1200
cgaaaatact tttcgctcac aaatgtatgc acaaattgat cgattcttta attgagttac    1260
atgtaacagg caacaagtaa aa                                              1282
```

<210> SEQ ID NO 10
<211> LENGTH: 1218
<212> TYPE: DNA
<213> ORGANISM: Picochlorum strain
<220> FEATURE:
<221> NAME/KEY: gene
<222> LOCATION: (1)..(1218)
<223> OTHER INFORMATION: delta-12-desaturase 4 cDNA

<400> SEQUENCE: 10

```
cgcttctgtt gcggctcaag caggtgacaa aatggctcat atcaagaatg gaaatggaac      60
gaatgcacag gcggatgctg ccaagagaca gccgacaaac acgccagatt tcacgattgg     120
acaacttcgt aaagtcatcc ctgcgcactg ctttgagagg tctttggtca gatctctcct     180
gtatttgttg gtcgatcttt ccatgattgc catgttgtac gtggggtcga cgtatattga     240
ctctgtggag gattctaggg ttcggtatgg cgtgctgtgg cctctctact ggtttttcca     300
gggagctgtg gggaccgggg tgtgggtgct gtcgcacgag tgtggtcatc aggccttttc     360
aaagtaccag tgggtgaatg atggggttgg gttggtgttc cactccctcc tgttggtgcc     420
atactactca tggaagcatt cccacaggag gcatcattca aacactgggt ctgtggataa     480
ggatgaggtg tttgtgccca aggtgagaga tcgtgtgacg gaagacattg aatgggaaca     540
gtttggaccg tatcgattgg tcaagttgat gggatctctg ttgttgggtt ggcccatgta     600
tctcctgttc aatgtcaagt ccaggccata tcctggacat acgtgggtca accatttcga     660
```

```
tccatggtct ccaatcttca gtaagcgtga aaggattgaa gtggcagtga gcgatgtatc    720

cctggtggct gttatctatg gcttgtatag ggctggcgag acatggggat ggggttggtt    780

ggtgaagaca tatggcattc catacctgat tgtcaacttc tggttggtca tgattacctt    840

gctgcagcac acgcatcctt ctctccctca ttatacagac tcagagtggg attggctccg    900

gggtgccctg gcaactgtgg acaggaacta tggatggctt ttgaatacct tgcatcatca    960

tattgcagat acccacgtca cccaccatct cttctctcag atgcctcatt atcatgcaca   1020

agaagcaacc gaagcattga agcctatact gggaaagtat taccaaaagg atgatcggtt   1080

tatattcaaa gccttgtggc aagactatgc tgcatgcaga tatgtagccc cagatgtcgc   1140

aggcagtggt atcctgtggc agagagcatg atacatgtat tattctttat ttcctttttg   1200

taaatatctg gattgatt                                                 1218
```

```
<210> SEQ ID NO 11
<211> LENGTH: 1291
<212> TYPE: DNA
<213> ORGANISM: Picochlorum strain
<220> FEATURE:
<221> NAME/KEY: gene
<222> LOCATION: (1)..(1291)
<223> OTHER INFORMATION: delta-15-omega-3-desaturase cDNA

<400> SEQUENCE: 11

ccccttccct gcgttccaga atttctagga ctgggttggt gtctgttgcg gctccagtgg     60

agatttcacc agaagagaag cccgtgtttg agggtggaag aaagttagcc aacgccccac    120

cgttcactct tcaagatttg cgcgctgcta ttccaaaaga atgttttgag aagaatgtat    180

ttcaatcctt tgcctacctt gccctggatg tcggtattgt ggctgccctg gcctacggag    240

catacgcttt gaacaaccca ctcgtatggc ctctgtactg gttcgctcaa ggaacaatgt    300

tctgggctct gtttgttgtt ggacacgatt gtggacacca gagtttcagt tcaaacaagg    360

cgctgaatga ttttgttgga aacgttgtgc actcgtccat catggtgcca tatcacggat    420

ggaggattag ccatagaacc catcatgcca accatggcca tgtggagaat gacgagtctt    480

ggactccagt gacaaagagc cagttgactg gcatggacaa acttgccaag ttgggtcgcc    540

tcttgttccc aatgccattg tttgcctacc cgttctacct cttcaaccgc tccccaggga    600

agaatggatc tcactttgat ccaaagtctg atttgttcgt gccaggagag gaaaacatga    660

tcaagacatc aaacgcattc cagttgggat tcatcggaat tttggcagcg tgcacatttg    720

cacttggtcc aatggccatg ttcaagttgt atgtgttgcc atactggatg tttgttgtct    780

ggcttgatgt tgtgacatac cttcaccatc atgggccatc cgacccagaa gaagagatcc    840

catggtatag aaatgatgag tgggattaca tgagaggagg actgtccacc attgatcgtg    900

actatggaat tttcaataag attcatcatg atatcggaac acatgtggtg catcatttgt    960

tcccacaaat tccacactac cacttgtgca aagctactga tgctgtgaaa ccagtcatgg   1020

gtgaatatta cagagagcca gagccatctc ctggtccact cccaactcac ttgattggac   1080

cattggtgag gtcgtttgga aaggatcact atgttgatga cgaaggagac atcgtgttct   1140

acaagaagga tcctagtgtt tcattgtttt aacgtatggc tgaattaatt ctttcattca   1200

ggtgattcta caaccaattc tgctcaacaa gatgtcattt tttcgttcac tgtaaaacat   1260

tattaaaata atggtgtgta aagaaacgaa t                                  1291
```